US011424019B2

(12) United States Patent
Mimassi

(10) Patent No.: US 11,424,019 B2
(45) Date of Patent: Aug. 23, 2022

(54) SYSTEM AND METHODS FOR PERSONAL FOOD ITEM CUSTOMIZATION

(71) Applicant: RockSpoon, Inc., San Jose, CA (US)

(72) Inventor: Nagib Georges Mimassi, Palo Alto, CA (US)

(73) Assignee: ROCKSPOON, INC., San Jose, CA (US)

( * ) Notice: Subject to any disclaimer, the term of this patent is extended or adjusted under 35 U.S.C. 154(b) by 0 days.

(21) Appl. No.: 17/113,902

(22) Filed: Dec. 7, 2020

(65) Prior Publication Data
US 2021/0225490 A1 Jul. 22, 2021

Related U.S. Application Data

(60) Provisional application No. 62/964,446, filed on Jan. 22, 2020.

(51) Int. Cl.
*G16H 20/60* (2018.01)
*G16H 10/60* (2018.01)
*G16H 50/70* (2018.01)
*G16H 40/67* (2018.01)
*G16H 50/30* (2018.01)
*G06Q 30/06* (2012.01)
*G06Q 50/12* (2012.01)
*A61B 5/145* (2006.01)

(52) U.S. Cl.
CPC ......... *G16H 20/60* (2018.01); *G06Q 30/0621* (2013.01); *G06Q 30/0631* (2013.01); *G06Q 50/12* (2013.01); *G16H 10/60* (2018.01); *G16H 40/67* (2018.01); *G16H 50/30* (2018.01); *G16H 50/70* (2018.01); *A61B 5/14532* (2013.01)

(58) Field of Classification Search
CPC ........ G16H 20/60; G16H 10/60; G16H 50/70; G16H 40/67; G16H 50/30; G06Q 30/0631; G06Q 30/0621; G06Q 50/12; A61B 5/14532
See application file for complete search history.

(56) References Cited

U.S. PATENT DOCUMENTS

| 6,038,546 | A  | * | 3/2000  | Ferro      | G06Q 50/12 705/15 |
| 6,865,261 | B1 | * | 3/2005  | Rao        | H04W 92/02 379/93.12 |
| 7,421,285 | B1 | * | 9/2008  | Rao        | H04W 40/02 455/557 |
| 7,638,148 | B2 | * | 12/2009 | Lahteenmaki | A23L 2/38 424/770 |
| 8,560,334 | B2 | * | 10/2013 | Lahteenmaki | G06Q 50/00 705/2 |
| 9,519,901 | B1 |   | 12/2016 | Dorogusker |            |

(Continued)

*Primary Examiner* — Michael Collins
(74) *Attorney, Agent, or Firm* — Galvin Patent Law LLC; Brian R. Galvin

(57) ABSTRACT

A user health profile is created at a personal food item customization system. The personal food item customization system receives a food item recipe including a plurality of ingredients, identifies at least one ingredient that includes a nutritional value that places the food item outside of a nutritional parameter range in the user health profile, modifies one or more identified ingredients in the food item recipe to bring the nutritional value of the nutrient in the food item within the nutritional parameter range, and generates a user specific food item recipe.

20 Claims, 9 Drawing Sheets

(56) References Cited

U.S. PATENT DOCUMENTS

| | | | |
|---|---|---|---|
| 10,671,705 B2 | 6/2020 | Capell et al. | |
| 10,720,235 B2 | 7/2020 | Leifer et al. | |
| 2003/0182160 A1* | 9/2003 | Lahteenmaki | A61J 3/002 705/2 |
| 2005/0048461 A1* | 3/2005 | Lahteenmaki | G16B 50/00 435/3 |
| 2013/0218602 A1* | 8/2013 | Lahteenmaki | G06Q 10/10 705/3 |
| 2014/0080102 A1* | 3/2014 | Krishna | G06Q 30/02 434/127 |
| 2016/0048821 A1 | 2/2016 | Sprecher | |
| 2016/0306931 A1* | 10/2016 | Lahteenmaki | G16H 40/67 |
| 2017/0031966 A1 | 2/2017 | Bhatt et al. | |
| 2017/0103676 A1 | 4/2017 | Allen et al. | |
| 2018/0342173 A1* | 11/2018 | Jordan | G16H 20/60 |
| 2019/0357819 A1 | 11/2019 | Yao | |
| 2020/0043593 A1 | 2/2020 | Alptekin et al. | |

* cited by examiner

SYSTEM AND METHODS FOR PERSONAL FOOD ITEM CUSTOMIZATION

CROSS-REFERENCE TO RELATED APPLICATIONS

| application Ser. No. | Date Filed | Title |
|---|---|---|
| Current application | Herewith | SYSTEM AND METHODS FOR PERSONAL FOOD ITEM CUSTOMIZATION Claims benefit of, and priority to: |
| 62/964,446 | Jan. 22, 2020 | PERSONAL FOOD ITEM CUSTOMIZATION SYSTEM AND METHOD THEREOF | the entire specification of each of which is incorporated herein by reference.

BACKGROUND

Many individuals suffer from health conditions that may benefit from dietary changes. Different health conditions often have recommended nutritional parameter ranges for the nutritional values associated with different nutrients. For example, if an individual suffers from a health condition of heart disease, the recommended nutritional parameter range for a nutrient, cholesterol, may be 0 mg to 200 mg.

Food item recipes for food items include one or more different ingredients. Each of the ingredients typically includes one or more different nutrients having associated nutritional values. In many cases, the food item recipes include ingredients with nutrients having nutritional values that place the food item outside of the recommended nutritional parameter range for nutrients that may adversely impact a health condition of an individual.

SUMMARY

Accordingly, the inventor has conceived and reduced to practice in preferred embodiments of the present invention, a system and methods for personal food item customization that enable patrons at a restaurant to easily tailor menu items or custom orders to suit their personal dietary, nutrition, or health requirements.

According to a preferred embodiment, one or more computer storage media include computer-executable instructions that, upon execution by a processor, cause the processor to: create a user health profile comprising a user health condition and a nutritional parameter range for nutritional values of a nutrient associated with the user health condition at a personal food item customization system, receive a food item recipe associated with a food item at the personal food item customization system, the food item recipe including a plurality of ingredients, identify at least one ingredient from the plurality of ingredients in the food item recipe that includes a nutritional value for the nutrient that places the food item outside of the nutritional parameter range at the personal food item customization system, modify one of more of the at least one identified ingredient in the food item recipe to bring the nutritional value of the nutrient in the food item within the nutritional parameter range at the personal food item customization system, and generate a user specific food item recipe associated with the food item based including the modified ingredients at the personal food item customization system.

According to another preferred embodiment, a computerized method includes creating a user health profile comprising a user health condition and a nutritional parameter range for nutritional values of a nutrient associated with the user health condition at a personal food item customization system, receiving a food item recipe associated with a food item at the personal food item customization system, the food item recipe including a plurality of ingredients, identifying at least one ingredient from the plurality of ingredients in the food item recipe that includes a nutritional value for the nutrient that places the food item outside of the nutritional parameter range at the personal food item customization system, modifying one of more of the at least one identified ingredient in the food item recipe to bring the nutritional value of the nutrient in the food item within the nutritional parameter range at the personal food item customization system, and generating a user specific food item recipe associated with the food item based including the modified ingredients at the personal food item customization system.

BRIEF DESCRIPTION OF THE DRAWING FIGURES

The accompanying drawings illustrate several aspects and, together with the description, serve to explain the principles of the invention according to the aspects. It will be appreciated by one skilled in the art that the particular arrangements illustrated in the drawings are merely exemplary and are not to be considered as limiting of the scope of the invention or the claims herein in any way.

DETAILED DESCRIPTION

Figure 1:
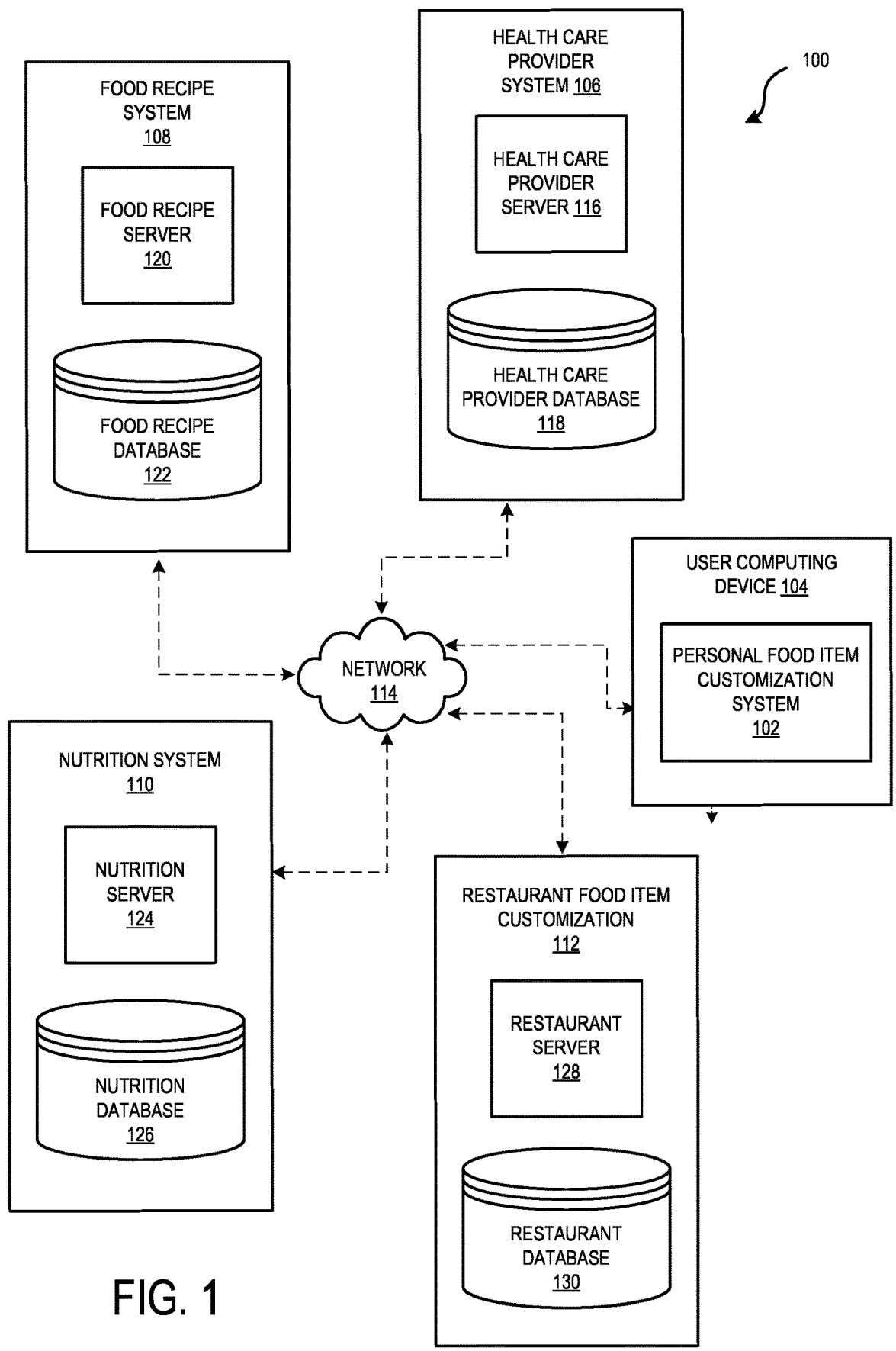
FIG. 1 is a block diagram representation of an exemplary architecture including an embodiment of a personal food item customization system.

The inventor has conceived and reduced to practice in preferred embodiments of the present invention, a system and methods for personal food item customization that enable patrons at a restaurant to easily tailor menu items or custom orders to suit their personal dietary, nutrition, or health requirements.

A personal food item customization system enables a user to customize food item recipes for food items by modifying the ingredients in the food item recipes to accommodate one or more user health conditions. The personal food item customization system creates a user health profile. The user health profile includes one or more user health conditions and a user nutritional profile. The user nutritional profile includes a list of nutrients that may impact the user health condition(s) and recommended nutritional parameter ranges for nutritional values of the nutrients.

The personal food item customization system receives a food item recipe for a food item selected by the user. The food item recipe includes one or more ingredients used to prepare the food item. The personal food item customization system retrieves the list of nutrients that may impact the user health condition(s) from the user nutritional profile, identifies one or more ingredients in the food item recipe that include a nutrient from the retrieved list of nutrients, and retrieves the nutritional parameter ranges for the nutrient(s) present in the identified ingredients from the user nutritional profile.

The personal food item customization system modifies one or more of the identified ingredients in the food item recipe that include a nutritional value for a nutrient on the list of nutrients that places the food item outside of the nutritional parameter range to bring the food item within the nutritional parameters range for the nutrient. The personal food item customization system may replace one or more of the ingredients in the food item recipe with a substitute ingredient and generate a user specific food item recipe for the food item. The personal food item customization system may reduce the amount of one or more of the ingredients in the food item recipe and generate a user specific food item recipe for the food item. The personal food item customization system stores the user specific food item recipe including the modified ingredient(s) at the personal food item customization system.

A user is provided with the option of using the personal food item customization system to coordinate with a restaurant food item customization system to identify restaurant food items at a restaurant that accommodate the user health condition(s). The personal food item customization system transmits the user nutritional profile to the restaurant food item customization system. The restaurant food item customization system creates a customer specific restaurant profile for the user based on the user nutritional profile and stores the customer specific restaurant profile at a restaurant database.

The personal food item customization system issues a request to the restaurant food item customization system for a list of restaurant food items with ingredients including nutrients having nutritional values that fall within the nutritional parameter range defined in the previously submitted user nutritional profile. The restaurant food item customization system retrieves the list of restaurant food items at the restaurant and the restaurant food item recipes for each of the restaurant food items including the ingredients in the restaurant food item recipes and the user nutritional profile from the customer specific restaurant profile from the restaurant database.

The restaurant food item customization system generates the requested list of restaurant food items. The restaurant food item customization system may generate a list of restaurant food items with ingredients including nutrients having nutritional values that fall within the nutritional parameter range defined in the retrieved user nutritional profile. The restaurant food item customization system may generate a list of restaurant food items with ingredients that can be modified by the restaurant to place the restaurant food items within the nutritional parameter range defined in the retrieved user nutritional profile. The restaurant food item customization system may generate a list of previously ordered restaurant food items with ingredients that can be modified by the restaurant to place the previously ordered restaurant food items within the nutritional parameter range defined in the retrieved user nutritional profile. The restaurant food item customization system transmits the list of restaurant food items to the personal food item customization system for presentation to the user.

One or more different aspects may be described in the present application. Further, for one or more of the aspects described herein, numerous alternative arrangements may be described; it should be appreciated that these are presented for illustrative purposes only and are not limiting of the aspects contained herein or the claims presented herein in any way. One or more of the arrangements may be widely applicable to numerous aspects, as may be readily apparent from the disclosure. In general, arrangements are described in sufficient detail to enable those skilled in the art to practice one or more of the aspects, and it should be appreciated that other arrangements may be utilized and that structural, logical, software, electrical and other changes may be made without departing from the scope of the particular aspects. Particular features of one or more of the aspects described herein may be described with reference to one or more particular aspects or figures that form a part of the present disclosure, and in which are shown, by way of illustration, specific arrangements of one or more of the aspects. It should be appreciated, however, that such features are not limited to usage in the one or more particular aspects or figures with reference to which they are described. The present disclosure is neither a literal description of all arrangements of one or more of the aspects nor a listing of features of one or more of the aspects that must be present in all arrangements.

Headings of sections provided in this patent application and the title of this patent application are for convenience only, and are not to be taken as limiting the disclosure in any way.

Devices that are in communication with each other need not be in continuous communication with each other, unless expressly specified otherwise. In addition, devices that are in communication with each other may communicate directly or indirectly through one or more communication means or intermediaries, logical or physical.

A description of an aspect with several components in communication with each other does not imply that all such components are required. To the contrary, a variety of optional components may be described to illustrate a wide variety of possible aspects and in order to more fully illustrate one or more aspects. Similarly, although process steps, method steps, algorithms or the like may be described in a sequential order, such processes, methods and algorithms may generally be configured to work in alternate orders, unless specifically stated to the contrary. In other words, any sequence or order of steps that may be described in this patent application does not, in and of itself, indicate a requirement that the steps be performed in that order. The steps of described processes may be performed in any order practical. Further, some steps may be performed simultaneously despite being described or implied as occurring non-simultaneously (e.g., because one step is described after the other step). Moreover, the illustration of a process by its depiction in a drawing does not imply that the illustrated process is exclusive of other variations and modifications thereto, does not imply that the illustrated process or any of its steps are necessary to one or more of the aspects, and does not imply that the illustrated process is preferred. Also, steps are generally described once per aspect, but this does not mean they must occur once, or that they may only occur once each time a process, method, or algorithm is carried out or executed. Some steps may be omitted in some aspects or some occurrences, or some steps may be executed more than once in a given aspect or occurrence.

When a single device or article is described herein, it will be readily apparent that more than one device or article may be used in place of a single device or article. Similarly, where more than one device or article is described herein, it will be readily apparent that a single device or article may be used in place of the more than one device or article.

The functionality or the features of a device may be alternatively embodied by one or more other devices that are not explicitly described as having such functionality or features. Thus, other aspects need not include the device itself.

Techniques and mechanisms described or referenced herein will sometimes be described in singular form for clarity. However, it should be appreciated that particular aspects may include multiple iterations of a technique or multiple instantiations of a mechanism unless noted otherwise. Process descriptions or blocks in figures should be understood as representing modules, segments, or portions of code which include one or more executable instructions for implementing specific logical functions or steps in the process. Alternate implementations are included within the scope of various aspects in which, for example, functions may be executed out of order from that shown or discussed, including substantially concurrently or in reverse order, depending on the functionality involved, as would be understood by those having ordinary skill in the art.

Conceptual Architecture

Referring to FIG. 1, a block diagram representation of an example of an architecture 100 including an embodiment of a personal food item customization system 102 is shown. The personal food item customization system 102 may be configured to operate on a user computing device 104. Examples of user computing devices 104 include, but are not limited to, a mobile computing device, a cell phone, a desktop computer, and a tablet. Personal food item customization system 102 is configured to be communicatively coupled to one or more of a health care provider system 106, a food recipe system 108, and a nutrition system 110, and a restaurant food item customization system 112 via a network 114. Examples of the network 114 include, but are not limited to, the Internet and a local area network.

Personal food item customization system 102 may be configured to maintain a user health profile. The user health profile may include a user identifier, one or more user specific parameters, one or more user health conditions, and a user nutritional profile. Examples of user specific parameters include, but are not limited to, a user height, a user weight, and a user activity level. According to the embodiment, the user provides the food personal food item customization system 102 with the user specific parameters via an input of the user computing device 104.

According to an embodiment, the user health condition(s) is a current user health condition. Personal food item customization system 102 is configured to be communicatively coupled to the health care provider system 106 via the network 114. Health care provider system 106 may include a health care provider server 116 and a health care provider database 118. The health care provider database 118 may include user specific health records associated with the user. The user specific health records include one or more current user health conditions associated with the user. Upon authorization by the user, the personal food item customization system 102 is configured to retrieve the current user health conditions from the health care provider system 106. The retrieved current user health conditions are added to the user health profile at the personal food item customization system 102.

According to another embodiment, the user health condition(s) is a potential user health condition. Personal food item customization system 102 is configured to be communicatively coupled to health care provider system 106 via the network 114. Health care provider system 106 may include a health care provider server 116 and a health care provider database 118. Health care provider database 118 may include user specific health records associated with the user. User-specific health records include one or more potential user health conditions associated with the user. Upon authorization by the user, personal food item customization system 102 is configured to retrieve the potential user health conditions from the health care provider system 106. The retrieved potential user health conditions are added to the user health profile of the personal food item customization system 102.

According to another embodiment, the user health condition(s) is a user goal-based health condition. A user provides the personal food item customization system 102 with one or more user goal-based health conditions. For example, a user may have a user goal-based health condition to increase muscle mass. The user goal-based health condition is added to the user health profile at the personal food item customization system 102. According to the embodiment, the user health condition(s) in the user health profile may include one or more of a current user health condition(s), a potential user health condition(s), and a user goal-based health condition(s).

Personal food item customization system 102 may be configured to maintain a user nutritional profile as a part of the user health profile. A food item recipe for a food item may include one or more ingredients. Each of the ingredients typically includes one or more different nutrients having associated nutritional values. The user nutritional profile may include one or more recommended nutritional parameter ranges for the nutritional values associated with different nutrients that may be present in the ingredients of food item recipes. The recommended nutritional parameter ranges for the nutritional values associated with the different nutrients are specific to the user health conditions in the user health profile.

According to an embodiment, personal food item customization system 102 may be configured to be communicatively coupled to the health care provider system 106 via the network 114. Health care provider system 106 may include a health care provider server 116 and a health care provider database 118. Health care provider database 118 may include recommended nutritional parameter ranges for nutritional values associated with different nutrients for individuals having specific health conditions. For example, health care provider database 118 may include a recommended nutritional parameter range of 0 mg to 200 mg for the nutrient, cholesterol, for individuals having a user health condition of heart disease. Upon receipt of a user health condition at the personal food item customization system 102, personal food item customization system 102 retrieves the recommended nutritional parameter ranges for the nutritional values associated with the nutrients that may impact the received user health condition. Retrieved nutritional parameter ranges for the nutritional values associated with the different nutrients are maintained in the user nutritional profile.

According to another embodiment, personal food item customization system 102 may be configured to be communicatively coupled to the food recipe system 108 via network 114. Food recipe system 108 may include a food recipe server 120 and a food recipe database 122. Food recipe database 120 may include food item recipes for different food items. Each food item recipe may include one or more ingredients and one or more food item preparation techniques to prepare the food item. A user is provided with the option of selecting one or more food item recipes from the food recipe system 108 for processing by the personal food item customization system 102.

According to another embodiment, personal food item customization system 102 may be configured to be communicatively coupled to a nutrition system 110. Nutrition system 110 may include a nutrition server 124 and a nutrition database 126. A food item recipe for a food item may include one or more ingredients. Each of the ingredients in a food item recipe typically includes one or more different nutrients. Nutrition database 126 may include nutritional values for different nutrients that may be present in different ingredients. For example, a food item recipe may include an egg as an ingredient. Eggs include a nutrient cholesterol and the nutritional value for the nutrient, cholesterol, in an egg is 186 mg. Upon the selection of a food item recipe for a food item by a user, the personal food item customization system 102 identifies the ingredients in the food item recipe and retrieves the nutritional values associated with the different nutrients present in the identified ingredients from the nutrition system 110. Personal food item customization system 102 extracts the nutrient values for the nutrients associated with the nutritional parameter ranges associated with the different nutrients that are maintained in the user nutritional profile.

According to another embodiment, personal food item customization system 102 may be configured to be communicatively coupled to a restaurant food item customization system 112 via network 114. Restaurant food item customization system 112 may be associated with a restaurant and may include a restaurant server 128 and a restaurant database 130. Restaurant food item customization system 112 maintains customer specific restaurant profiles for customers of the restaurant, the restaurant food items served at the restaurant, the restaurant food item recipes of each of the restaurant food items served at the restaurant, and the ingredients in each of the restaurant food item recipes. Upon authorization by a customer, the user computing device 104 establishes a communication channel with restaurant food item customization system 112 and provides restaurant food item customization system 112 with one or more elements of the user health profile for addition to the customer specific restaurant profile for the user.

According to another embodiment, restaurant food item customization system 112 may utilize the received elements of the user health profile to provide the user with a restaurant food item list identifying the restaurant food items that fall within the nutritional parameter ranges for nutritional values associated with the nutrients defined in the user health profile via the personal food item customization system 102. Restaurant food item customization system 112 may utilize the received user health profile to provide the user with a restaurant food item list identifying the restaurant food items that can be modified by the restaurant to place the restaurant food items within the nutritional parameter ranges for nutritional values associated with the nutrients defined in the user health profile via personal food item customization system 102.

According to another embodiment, each of the customer specific restaurant profiles at restaurant food item customization system 112 may include a list of previously ordered restaurant food item. Restaurant food item customization system 112 utilizes the received elements of the user health profile to provide the user with the list of previously ordered restaurant food items identifying the specific previously ordered restaurant food items that can be modified by the restaurant to place the restaurant food items within the nutritional parameter range for the nutritional values associated with the nutrients defined in the user health profile via personal food item customization system 102.

According to another embodiment, personal food item customization system 102 may be configured to receive pre-meal user biometric data prior to the consumption of a food item prepared in accordance with a user specific food item recipe generated by personal food item customization system 102 and receive a post-meal user biometric data following the consumption of the food item prepared in accordance with the user specific food item recipe. Personal food item customization system 102 may provide feedback regarding changes in the user biometric data thereby enabling a user to determine whether the user specific food item recipe has accommodated the user health condition(s) detailed in the user health profile.

According to another embodiment, personal food item customization system 102 may be configured to receive user biometric data. Personal food item customization system 102 determines whether the received user biometric data warrants updating one or more nutritional parameter ranges for nutritional values associated with the nutrients in the user health profile in order to better accommodate a user heath condition. Personal food item customization system 102 updates one or more of the nutritional parameter ranges for nutritional values associated with the nutrients in the user health profile based on the determination.

According to another embodiment, personal food item customization system 102 may be configured to make recommendations to a user regarding food purchases based on the user health condition profile. Personal food item customization system 102 may be configured to track food purchases and make recommendations regarding substitute food purchases based on a user provided food budget.

While an architecture 100 including an embodiment of a personal food item customization system 102 including one or more of a health care provider system 106, food recipe system 108, and a nutrition system 110, and a restaurant food item customization system 112 has been described, the architecture 100 may include additional components that facilitate the operation of the personal food item customization system 102.

Figure 2:
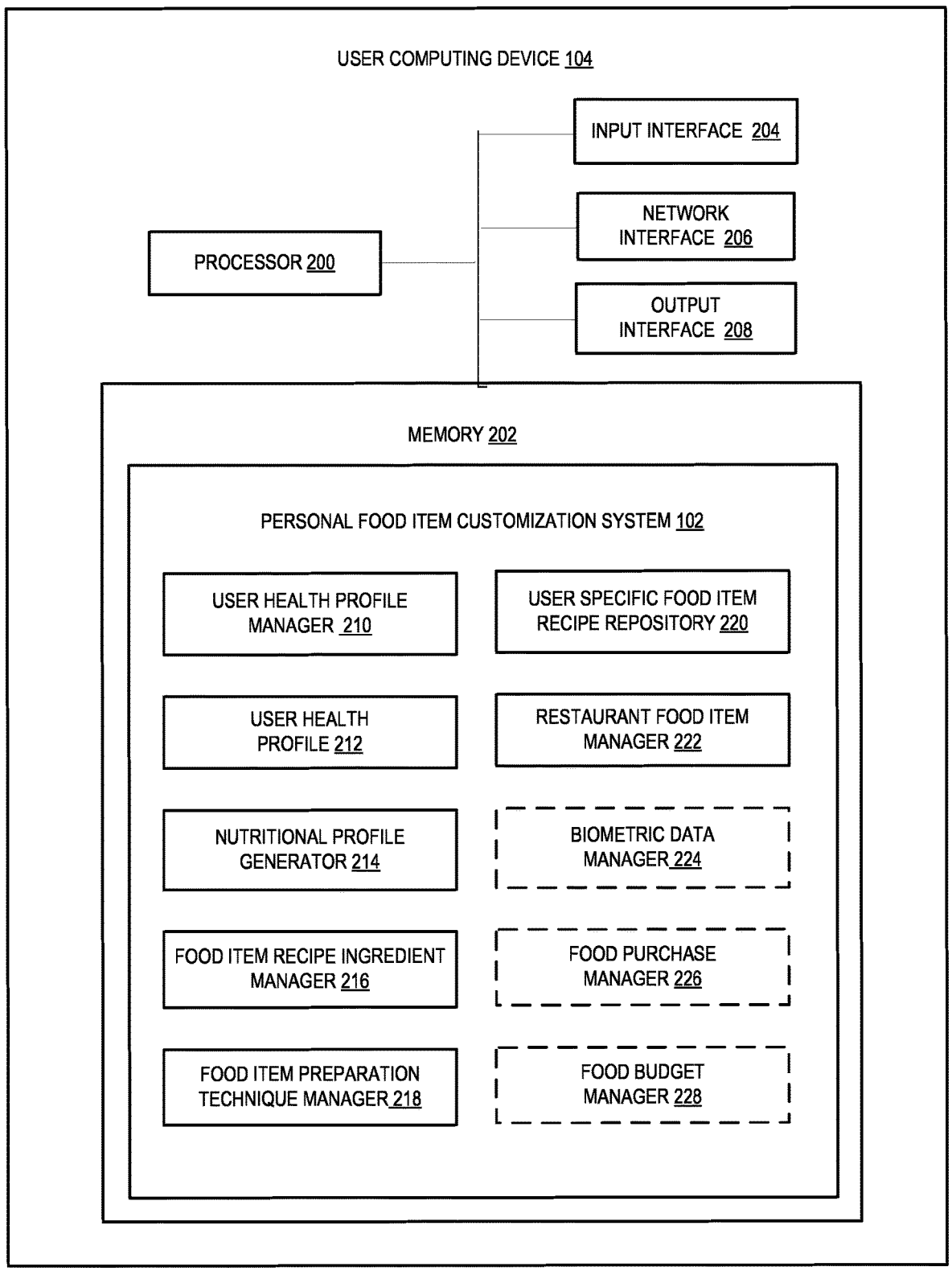
FIG. 2 is a block diagram representation of an example of a user computing device including an embodiment of a personal food item customization system.

Referring now to FIG. 2, an example of a user computing device 104 including an embodiment of a personal food item customization system 102 is shown. User computing device 104 may include a processor 200, a memory 202, at least one input interface 204, at least one network interface 206, and at least one output interface 208. Processor 200 may be communicatively coupled to the memory 202, the at least one input interface 204, the at least one network interface 206 and the at least one output interface 208. According to an embodiment, the memory 202 may include the personal food item customization system 102 described previously (referring to FIG. 1). While a number of different components of a user computing device 104 have been described, user computing device 104 may include additional components that facilitate operation of user computing device 104.

Personal food item customization system 102 may include one or more of a user health profile manager 210, the user health profile 212, a nutritional profile generator 214, a food item recipe ingredient manager 216, a food item preparation technique manager 218, a user specific food item recipe repository 220, a restaurant food item manager 222, a biometric data manager 224, a food purchase manager 226, and a food budget manager 228. In an embodiment, the personal food item customization system 102 may include the user health profile manager 210, the user health profile 212, a nutritional profile generator 214, the food item recipe ingredient manager 216, the food item preparation technique manager 218, the user specific food item recipe repository 220, and the restaurant food item manager 222. The personal food item customization system 102 may include additional components that facilitate the operation of the personal food item customization system 102.

User health profile manager 210 generates the user health profile 212 and manages updates to the user health profile 212. User health profile 212 may include the user identifier, one or more user specific parameters, one or more user health conditions, and the user nutritional profile. Upon the initiation of personal food customization system 102, user health profile manager 210 prompts the user to enter a user identifier and user specific parameters. An example of a user identifier is a name of the user. Examples of user specific parameters include but are not limited to user height, user weight, and user activity level. The user health profile manager 210 generates the user health profile using the user identifier and the user specific parameters.

According to an embodiment, upon authorization by the user, user health profile manager 210 may establish a communication channel with the health care provider system 106. Health care provider database 118 may include user specific health records associated with the user. The user specific health records include one or more user health conditions associated with the user. In an embodiment, the one or more user health conditions include one or more current user health conditions. Current user health conditions may, for example, be health conditions that have already been diagnosed by a health care professional. Examples of current user health conditions include, but are not limited to, high blood pressure, diabetes, heart disease, and allergies. User health profile manager 210 retrieves the current user health conditions in the user specific health records from health care provider system 106 and adds the retrieved current user health conditions to user health profile 212 at the personal food item customization system 102.

According to another embodiment, one or more user health conditions may include potential user health conditions. Potential user health conditions may, for example, be health conditions that the user may have at some time in the future. Potential user health conditions may be based on a family history. Examples of potential user health conditions include, but are not limited to high blood pressure, diabetes, and heart disease. User health profile manager 210 retrieves the potential user health conditions in the user specific health records from the health care provider system 106 and adds the retrieved potential user health conditions to the user health profile 212 at personal food item customization system 102.

According to another embodiment, one or more user health conditions may include user goal-based health conditions. User goal-based health conditions may, for example, be based on target health conditions that the user wishes to reach. For example, a user may have a user goal-based health condition to increase muscle mass. User health profile manager 210 prompts the user to enter one or more user goal-based health conditions. The user provides one or more user goal-based health conditions. The user health profile manager 210 adds the received one or more user goal-based health conditions to the user health profile 212.

User health profile 210 may include a user nutritional profile. Nutritional profile generator 214 generates user nutritional profile and manages updates to the user nutritional profile. A food item recipe for a food item may include one or more ingredients. Each of the ingredients typically includes one or more different nutrients having associated nutritional values. The user nutritional profile may include one or more recommended nutritional parameter ranges for the nutritional values associated with different nutrients that may be present in the ingredients of food item recipes. The recommended nutritional parameter ranges for the nutritional values associated with the different nutrients are specific to the user health conditions in the user health profile 212.

According to another embodiment, health care provider database 118 of the health care provider system 106 may include recommended nutritional parameter ranges for nutritional values associated with different nutrients for individuals having specific health conditions. For example, the health care provider database 118 may include a recommended nutritional parameter range of 0 mg to 200 mg for the nutrient, cholesterol, for individuals having a health condition of heart disease. Upon the receipt of a user health condition at the user health profile 212, the nutritional profile generator 214 establishes a communication channel with the health care provider system 106 and retrieves the recommended nutritional parameter ranges for the nutritional values associated with the nutrients that may impact the received user health condition from the health care provider system 106. Nutritional profile generator 214 adds the retrieved nutritional parameter ranges for the nutritional values associated with the different nutrients to the user nutritional profile. The user nutritional profile maintains a listing of the nutrients that have been identified as potentially impacting the one or more user health conditions in the user health profile 212.

According to another embodiment, food recipe system 108 may include the food recipe server 120 and the food recipe database 122. The food recipe database 122 may include food item recipes for different food items. Each food item recipe may include one or more ingredients and one or more food item preparation techniques to prepare the food item. The user is provided with the option of selecting one or more food items from the food recipe system 108 via the user computing device 104. The food item recipe ingredient manager 216 receives the food item recipe for the user selected food item.

Upon receipt of a food item recipe associated with the user selected food item from food recipe system 108, food item recipe ingredient manager 216 retrieves the list of nutrients that may potentially impact the one or more health conditions from the user nutritional profile. Food item recipe ingredient manager 216 determines whether any of the ingredients in the received food item recipe includes one of more of nutrients in the retrieved list of nutrients. If the food item recipe ingredient manager 216 identifies one or more ingredients in the food item recipe that includes a nutrient from the list of nutrients, the food item recipe ingredient manager 216 retrieves the nutritional parameter range for the nutrient from the user nutritional profile.

For example, a user having a user health condition of heart disease in a user health profile 212 may select a pan seared strip steak as a food item from food recipe system 108. The ingredients in the food item recipe for the food item, pan seared strip steak, may include an 8 oz portion of strip steak, salt, pepper, and four tablespoons of butter. Food item recipe ingredient manager 216 retrieves the list of nutrients from the user nutritional profile. The user nutritional profile may include cholesterol as a nutrient that may potentially impact the user health condition of heart disease and may include a recommended nutritional parameter range of 0 mg to 200 mg for the nutrient, cholesterol, for individuals having a health condition of heart disease. Food item recipe ingredient manager 216 identifies ingredients, an 8 oz portion of strip steak and the four tablespoons of butter, as including the nutrient cholesterol. Food item recipe ingredient manager 216 may determine that the 8 oz portion of strip steak has a nutritional value of 130 mg for the nutrient, cholesterol, and that the four tablespoons of butter has a nutritional value of 124 mg for the nutrient, cholesterol, thereby bringing the total nutritional value for the nutrient, cholesterol, for the food item recipe for the food item, pan seared strip steak to 254 mg. The food item recipe ingredient manager 216 determines that the nutritional value of 254 mg for the nutrient, cholesterol, falls outside of the retrieved nutritional parameter range of 0 mg to 200 mg.

Food item recipe ingredient manager 216 may then modify one or more of the ingredients in the food item recipe that includes the nutrient that places the food item outside of the nutritional parameter range for that nutrient and generates a user specific food item recipe for the food item. Food item recipe ingredient manager 216 replaces the one or more of the ingredients in the food item recipe that includes the nutrient that places the food item outside of the nutritional parameter range for that nutrient with a substitute ingredient and generates a user specific food item recipe for the food item. Food item recipe ingredient manager 216 stores the user specific food item recipe including the modified one or more ingredients in the user specific food item recipe repository 220.

As another example, with respect to the food item recipe for the food item, pan seared strip steak, food item recipe ingredient manager 216 may replace the four tablespoons of butter with a substitute ingredient of four tablespoons of olive oil. The user specific food item recipe for the pan seared strip steak would have a nutritional value of 130 mg for the nutrient, cholesterol, and fall within the nutritional parameter range of 0 mg to 200 mg. The food item recipe ingredient manager 216 stores the user specific food item recipe for the food item, pan seared strip steak, in the user specific food item recipe repository 220. Food item recipe ingredient manager 216 may reduce the amount of one or more of the ingredients in the food item recipe that includes the nutrient that places the food item outside of the nutritional parameter range for that nutrient and generates a user specific food item recipe for the food item. The food item recipe ingredient manager 216 stores the user specific food item recipe including the reduced amounts of the one or more ingredients in the user specific food item recipe repository 220.

As another example, with respect to a food item recipe for a food item, pan seared strip steak, food item recipe ingredient manager 216 may reduce the portion of the strip steak from an 8 oz portion to 4 oz portion, thereby reducing the nutritional value for the nutrient, cholesterol, in the strip steak portion from 130 mg to 65 mg and generate a user specific food item recipe for the pan seared strip steak. The user specific food item recipe for the pan seared strip steak would have a nutritional value of 189 mg for the nutrient, cholesterol, and fall within the nutritional parameter range of 0 mg to 200 mg. Food item recipe ingredient manager 216 may store the user specific food item recipe for the food item, pan seared strip steak, in the user specific food item recipe repository 220.

According to another embodiment, food item recipe ingredient manager 216 determines whether addition of a potential ingredient positively impacts a user health condition in the user health profile. If food item recipe ingredient manager 216 determines that the addition of a specific ingredient may positively impacts the user health condition, food item recipe ingredient manager 216 adds the potential ingredient to the ingredients in the food item recipe and generates a user specific food item recipe for the food item. Food item recipe ingredient manager 216 stores the user specific food item recipe including the potential ingredient in a user specific food item recipe repository 220.

For example, consumption of avocados may lower low density lipoprotein (LDL) cholesterol levels and positively impact a user health condition of heath disease. With respect to the above example of a food item recipe for the food item, pan seared strip steak, Food item recipe ingredient manager 216 may add avocado as a potential ingredient to the food item recipe to be served as a topping for the pan seared strip steak and generate a user specific food item recipe. Food item recipe ingredient manager 216 stores the user specific food item recipe including avocado as a potential ingredient in the user specific food item recipe repository 220.

According to another embodiment, upon the receipt of the food item recipe associated with the user selected food item from food recipe system 108, food item preparation technique manager 218 retrieves the list of nutrients that may potentially impact the one or more user health conditions from the user nutritional profile. Food item preparation technique manager 218 determines whether the food item preparation technique used to prepare the food item involves a nutrient on the retrieved list of nutrients. If food item preparation technique manager 218 determines that the food item preparation technique used to prepare the food item involves a nutrient from the retrieved list of nutrients, food item preparation technique manager 218 retrieves the nutritional parameter range for the nutrient from the user nutritional profile. Food item preparation technique manager 218 modifies the food item preparation technique for the food item to bring the nutrient in the food item within the nutritional parameter range for that nutrient and generates a user specific food item recipe incorporating the modified food item preparation technique. Food item preparation technique manager 218 stores the user specific food item recipe including the modified food item preparation technique in a user specific food item recipe repository 220.

As another example, a user having a user health condition of heart disease in their respective user health profile 212 may select a pan seared strip steak as a food item from the food recipe system 108. Food item preparation technique manager 218 may determine that the 8 oz portion of strip steak having a nutritional value of 130 mg for the nutrient cholesterol is seared in a pan with four tablespoons of butter having a nutritional value of 124 mg for the nutrient cholesterol thereby bringing the total nutritional value for the nutrient cholesterol for the food item, the pan seared strip steak to 254 mg. Food item preparation technique manager 218 may determine that the nutritional value of 254 mg for the nutrient, cholesterol, falls outside of the retrieved nutritional parameter range of 0 mg to 200 mg and may recommends a modified food item preparation technique of broiling the strip steak in the oven and generate a user specific food item recipe with the modified food item preparation technique for the pan seared strip steak. The user specific food item recipe for the broiled strip steak would have a nutritional value of 130 mg for the nutrient, cholesterol and fall within the nutritional parameter range of 0 mg to 200 mg. Food item preparation technique manager 218 stores the user specific food item recipe for the food item pan seared strip steak with the modified food item preparation technique, broiling, in the user specific food item recipe repository 220.

According to another embodiment, personal food item customization system 102 may include a restaurant food item manager 222. Restaurant food item manager 222 enables a user to coordinate with a restaurant food item customization system 112 via the user computing device 104 to place an order for restaurant food items that accommodate the user health condition(s). Restaurant food item customization system 112 is associated with a specific restaurant.

Figure 3:
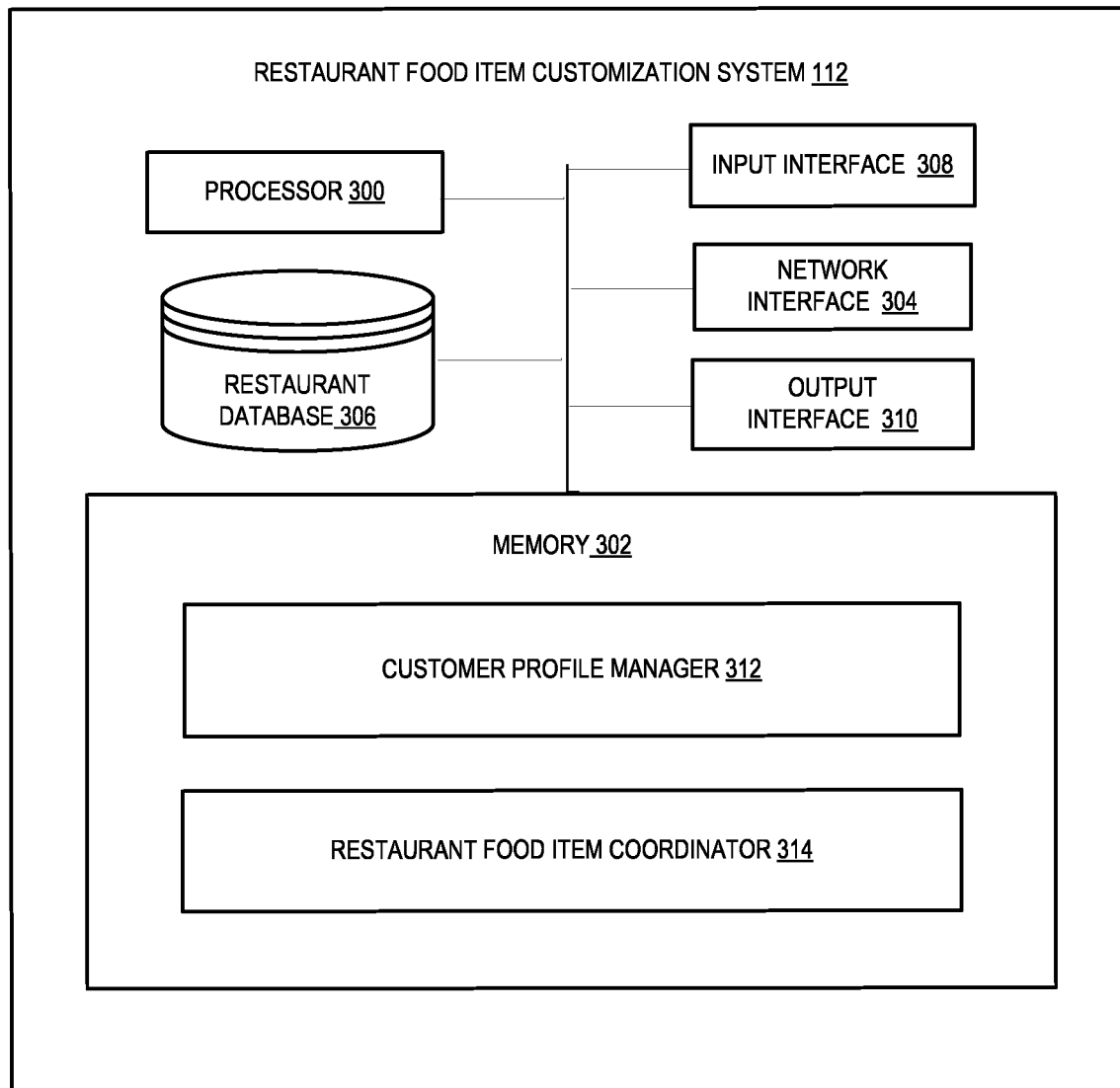
FIG. 3 is a block diagram representation of an embodiment of a restaurant customer food item customization system.

Referring now to FIG. 3, an embodiment of a restaurant food item customization system 112 is shown. Restaurant food item customization system 112 may include a processor 300, a memory 302, at least one network interface 304, and a restaurant database 306. The processor 300 is communicatively coupled to the memory 302, the at least one network interface 304 and the restaurant database 306. Restaurant food item customization system 112 may also include one or more of an at least one input interface 308 and at least one output interface 310. The processor 300 is communicatively coupled to one or more of the at least one input interface 308 and the at least one output interface 310. According to a preferred embodiment, the memory 302 may include a customer profile manager 312 and a restaurant food item coordinator 314. A listing of the restaurant food items available for order at the restaurant, the restaurant food item recipes for ach of the restaurant food items, the ingredients in each of the restaurant food item recipes and customer specific restaurant profiles for restaurant customers are stored in the restaurant database 306. While a number of different components of the restaurant food item customization system 112 have been described, the restaurant food item customization system 112 may include additional components that facilitate the operation of the restaurant food item customization system 112.

Referring to FIG. 2 and FIG. 3, upon authorization by a user, restaurant food item manager 222 of personal food item customization system 102 may establish a communication channel with a restaurant food item customization system 112. Restaurant food item manager 222 transmits one or more elements of the user profile associated with the user to the restaurant food item customization system 112. The user profile may include the user identifier, the one or more user specific parameters, one or more user health conditions and the user nutritional profile. In an embodiment, the restaurant food item manager 222 transmits the user identifier and the user nutritional profile to restaurant food item customization system 112. The customer profile manager 312 at the restaurant food item customization system 112 receives the user identifier and the user nutritional profile and creates a customer specific restaurant profile. The customer profile manager 312 stores the user identifier and the user nutritional profile for the user in the customer specific profile associated with the user at the restaurant database 306.

According to another embodiment, upon authorization by a user, when the user computing device 104 detects that the user has entered the restaurant associated with the restaurant food item customization system 112, personal food item customization system 102 establishes a communication channel with the restaurant food item customization system 112. Restaurant food item manager 222 issues a request to the restaurant food item customization system 112 for a list of the restaurant food items with ingredients including nutrients having nutritional values that fall within the nutritional parameter range defined in the previously submitted user nutritional profile. Restaurant food item coordinator 314 of restaurant food item customization system 112 receives the request and responsively accesses a customer specific restaurant profile for the user stored at the restaurant database 306. The customer specific restaurant profile may include the user nutritional profile. Restaurant food item coordinator 314 retrieves the list of restaurant food items from the restaurant database 306 and identifies the restaurant food items with ingredients including nutrients having nutritional values that fall within the nutritional parameter ranges defined in the user nutritional profile. Restaurant customer food item customization system 112 transmits the identified restaurant food items to the user computing device 104. Restaurant food item manager 222 of the personal food item customization system 102 receives the identified restaurant food items and provides a listing of the identified restaurant food items via a display associated with the user computing device 104.

According to another embodiment, upon authorization by a user, when the user computing device 104 detects that the user has entered the restaurant associated with a restaurant food item customization system 112, personal food item customization system 102 establishes a communication channel with restaurant food item customization system 112. Restaurant food item manager 222 issues a request to the food item customization system 112 for a list of the restaurant food items with ingredients including nutrients having nutritional values that fall outside of the nutritional parameter range defined in the previously submitted user nutritional profile that can be modified by the restaurant to place the restaurant food items within the nutritional parameter range. Restaurant food item coordinator 314 of the restaurant food item customization system 112 receives the request and responsively accesses the customer specific restaurant profile for the user stored at the restaurant database 306. The customer specific restaurant profile for the user may include the user nutritional profile. The restaurant food item coordinator 314 retrieves the list of restaurant food items from the restaurant database 306 and identifies the restaurant food items with ingredients including nutrients having nutritional values that fall outside the nutritional parameter ranges defined in the user nutritional profile. Restaurant food item coordinator 314 identifies the restaurant food items from the retrieved list of restaurant food items including one or more of the ingredients that can be modified to bring the restaurant food items within the nutritional parameter ranges defined in the user nutritional profile. The restaurant food item coordinator 314 modifies one or more of the ingredients that place the each of the identified food item outside of the nutritional parameter range for that nutrient and generates a modified restaurant food item recipe for each of the identified the restaurant food item. The restaurant food item customization system 112 transmits the list of the restaurant food items that can be modified by the restaurant to place the food item within the nutritional parameter range to the user computing device 104. The restaurant food item manager 222 of the personal food item customization system 102 receives the list of the restaurant food items and provides a listing of the listing of the restaurant food items via a display associated with the user computing device 104.

For example, a user health profile 212 for a customer may include a user health condition of heart disease. The user nutritional profile may specify that the nutrient, cholesterol, may have a recommended nutritional parameter range of 0 mg to 200 mg for individuals having a health condition of heart disease. Upon the transmission of the user identifier and the user nutritional profile from the restaurant food item manager 222 of the personal food item customization system 102 to restaurant food item customization system 112, the customer profile manager 312 at the restaurant food item customization system 112 creates a customer specific restaurant profile for the user and stores the user identifier and the user nutritional profile specifying a recommended nutritional parameter range of 0 mg to 200 mg for the nutrient, cholesterol, for the user in the customer specific restaurant profile at the restaurant database 306. One of the restaurant food items may be a pan seared strip steak. The ingredients in the food item recipe for the restaurant food item, pan seared strip steak, may include an 8 oz portion of strip steak, salt, pepper, and four tablespoons of butter. The restaurant food item coordinator 314 identifies the ingredients, the 8 oz portion of strip steak and the four tablespoons of butter as including the nutrient, cholesterol. The restaurant food item coordinator 314 determines that the 8 oz portion of strip steak has a nutritional value of 130 mg for the nutrient, cholesterol, and that the four tablespoons of butter has a nutritional value of 124 mg for the nutrient cholesterol thereby bringing the total nutritional value for the nutrient, cholesterol, for the restaurant food item recipe for the restaurant food item, pan seared strip steak to 254 mg. The restaurant food item coordinator 314 determines that the nutritional value of 254 mg for the nutrient, cholesterol, falls outside of the retrieved nutritional parameter range of 0 mg to 200 mg.

According to another embodiment, restaurant food item coordinator 314 may replace one or more of the ingredients in the restaurant food item recipe that includes the nutrient that places the restaurant food item outside of the nutritional parameter range for that nutrient and generates a modified restaurant food item recipe for the restaurant food item. For example, with respect to the exemplary restaurant food item recipe above for the restaurant food item, pan seared strip steak, restaurant food item coordinator 314 may replace the four tablespoons of butter with a substitute ingredient of four tablespoons of olive oil. The modified restaurant food item recipe for the pan seared strip steak would have a nutritional value of 130 mg for the nutrient cholesterol and fall within the nutritional parameter range of 0 mg to 200 mg.

According to another embodiment, restaurant food item coordinator 314 may reduce the amount of one or more of the ingredients in the restaurant food item recipe that includes the nutrient that places the restaurant food item outside of the nutritional parameter range for that nutrient and generates a modified restaurant food item recipe for the restaurant food item. For example, with respect to the exemplary restaurant food item recipe above for the restaurant food item, pan seared strip steak, restaurant food item coordinator 314 may reduce the portion of the strip steak from an 8 oz portion to 4 oz portion, thereby reducing the nutritional value for the nutrient, cholesterol, in the strip steak portion from 130 mg to 65 mg and generate a modified restaurant food item recipe for the pan seared strip steak. The modified restaurant food item recipe for the pan seared strip steak would have a nutritional value of 189 mg for the nutrient, cholesterol and fall within the nutritional parameter range of 0 mg to 200 mg.

According to another embodiment, upon authorization by a user, the customer profile manager 312 may maintain a list of previously ordered restaurant food items in the customer specific restaurant profile. When the user places an order for one or more restaurant food items at the restaurant, the user identifier and a list of the ordered restaurant food items are entered into the restaurant food item customization system 112. The list of ordered restaurant food items is entered by restaurant personnel via an input device that is communicatively coupled to the restaurant food item customization system 112 via an input interface 308. The user identifier and the list of restaurant food items is received by the customer profile manager 312. Customer profile manager 312 uses the user identifier to locate the customer specific restaurant profile for the user and adds the list of restaurant food items to the list of previously ordered restaurant food items for the user.

According to another embodiment, upon authorization by a user, when the user computing device 104 detects that the user has entered the restaurant associated with the restaurant food item customization system 112, personal food item customization system 102 establishes a communication channel with restaurant food item customization system 112. Restaurant food item manager 222 issues a request to the restaurant customer food item customization system 112 for a list of previously ordered the restaurant food items with ingredients including nutrients having nutritional values that fall outside of the nutritional parameter range defined in the previously submitted user nutritional profile that can be modified by the restaurant to place the restaurant food items within the nutritional parameter range. The restaurant food item coordinator 314 of the restaurant customer food item customization system 112 receives the request and responsively accesses the customer specific restaurant profile for the user stored at the restaurant database 306. The customer specific restaurant profile may include the user nutritional profile for the user. The restaurant food item coordinator 314 retrieves the list of previously ordered restaurant food items from the customer specific user profile stored at the restaurant database 306 and identifies the previously ordered restaurant food items with ingredients including nutrients having nutritional values that fall outside the nutritional parameter ranges defined in the user nutritional profile. The restaurant food item coordinator 314 identifies the previously ordered restaurant food items from the retrieved list of restaurant food items including one or more of the ingredients that can be modified to bring the restaurant food items within the nutritional parameter ranges defined in the user nutritional profile. The restaurant food item coordinator 314 modifies one or more of the ingredients that place the each of the identified food items outside of the nutritional parameter range for that nutrient and generates a modified restaurant food item recipe for each of the identified previously ordered restaurant food items. The restaurant food item customization system 112 transmits the list of the previously ordered restaurant food items that can be modified by the restaurant to place the restaurant food item within the nutritional parameter range to the user computing device 104. The restaurant food item manager 222 of the personal food item customization system 102 receives the list of the modifiable previously ordered restaurant food items and provides the listing of the modifiable previously ordered restaurant food items via a display associated with the user computing device 104.

According to another embodiment, personal food item customization system 102 may include a biometric data manager 224. According to the embodiment, the user computing device 104 is configured to be communicatively coupled to a biometric sensor. In an embodiment the user computing device 104 may include a biometric sensor. The biometric data manager 224 receives user biometric data sensed by the biometric sensor. User biometric data may be entered by the user via an input device communicatively coupled to the input interface 204. The entered user biometric data is received by the biometric data manager 224.

According to another embodiment, the user may initiate sensing of pre-meal user biometric data by the biometric sensor prior to consumption of a food item prepared in accordance with a user specific food item recipe generated by the personal food item customization system 102. The user may use an external biometric data sensor to sense the pre-meal user biometric data and enters the sensed pre-meal user biometric data into the personal food item customization system 102. Biometric data manager 224 receives the pre-meal user biometric data.

According to another embodiment, the user may initiate sensing of post-meal user biometric data by the biometric sensor following consumption of the food item prepared in accordance with the user specific food item recipe generated by the personal food item customization system 102. The user may use an external biometric data sensor to sense the post-meal user biometric data and enters the post-meal user biometric data into the personal food item customization system 102. Biometric data manager 224 receives the post-meal user biometric data.

Biometric data manager 224 compares the pre-meal user biometric data with a pre-meal biometric data threshold and compares the post-meal user biometric data with a post-meal biometric data threshold. Biometric data manager 224 provides feedback regarding the user biometric data thereby enabling a user to determine whether the user specific food item recipe has accommodated the user health condition(s) detailed in the user health profile. Biometric data manager 224 provides the user with feedback via a display communicatively coupled to the input interface of the user computing device 104.

For example, a user may have a user health condition of diabetes. The user biometric data may be blood glucose levels. The recommended pre-meal blood glucose levels may be between 80 and 130 mg/dL (4.4 and 7.2 mmol/L). The recommended post-meal blood glucose levels may be less than 180 mg/dL (10.0 mmol/L) two hours after the meal. Biometric data manager 224 receive the pre-meal blood glucose level may perform a first comparison of the pre-meal blood glucose level to the recommended range of 80 and 130 mg/dL (4.4 and 7.2 mmol/L). Biometric data manager 224 may receive the post-meal blood glucose level and may perform a second comparison of the post-meal blood glucose level to determine whether the post-meal blood glucose level is below the recommended level of 180 mg/dL (10.0 mmol/L). Biometric data manager 224 provides feedback regarding the pre-meal blood glucose level and the post-meal blood glucose level to the user based on the first and second comparisons thereby enabling the user to determine whether the user specific food item recipe has accommodated the user health condition of diabetes.

According to another embodiment, personal food item customization system 102 is configured to receive user biometric data. Personal food item customization system 102 determines whether the received user biometric data warrants updating one or more nutritional parameter ranges for nutritional values associated with the nutrients in the user health profile in order to better accommodate a user heath condition. Personal food item customization system 102 updates one or more of the nutritional parameter ranges for nutritional values associated with the nutrients in the user health profile based on the determination.

According to another embodiment, personal food item customization system 102 may include a food purchase manager 226. Food purchase manager 226 maintains a user food purchase history. The user food purchase history may include a history of ingredients purchased by a user at, for example, a grocery store. According to the embodiment, upon authorization by the user, the user computing device 104 detects when a user enters a grocery store. The personal food item customization system 102 establishes a communication channel with a grocery store system and receives a list of ingredients purchased by the user upon completion of a food purchase transaction at the grocery store.

When a user is shopping, the user may provide a main ingredient that the user wishes to use in a food item recipe to the personal food item customization system 102 via the user computing device 104. The main ingredient is received by the food purchase manager 226. The food purchase manager 226 retrieves the user specific food item recipes that includes the main ingredient from the user specific food item recipe repository 220. The food purchase manager 226 compares the ingredients in each of the retrieved user specific food item recipes with the ingredients in the user food purchase history. The food purchase manager 226 identifies the user specific food item recipe that includes the highest percentage of ingredients in the user food purchase history. The food purchase manager 226 recommends the purchase of the ingredients in the identified user specific food item recipe.

According to another embodiment, personal food item customization system 102 may include a food budget manager 228. The user may provide a budget amount the user has budgeted for the purchase of grocery items for use as ingredients to prepare food items at, for example, a grocery store. Food budget manager 228 enables a user to track ingredient purchases to ensure that the user stays within the budget amount. In an embodiment, upon authorization by a user, food purchase manager 226 establishes a communication channel with the grocery store system. Grocery store system provides the food budget manager 228 with a list of the grocery items that are available for purchase at the grocery store and the grocery item price for each of the grocery items.

According to another embodiment, as a user selects grocery items for purchase, the user provides a food budget manager 228 with a grocery item identifier associated with the selected grocery item via the user computing device 104. According to the embodiment, each of the grocery items may include bar code. The user computing device 104 may include a bar code recognizer. The user scans the bar code for the grocery item using the user computing device 104. The scanned bar code is received by the food budget manager 228. The food budget manager 228 maintains a running total of the sum of the grocery item prices associated with each of the grocery items selected by the user. The food budget manager 228 compares the running total with the budget amount and provides an alert to the user via the user computing device 104 when the running total reaches or exceeds the budget amount.

According to another embodiment, a grocery store system provides a food budget manager 228 with the nutrients and the values of the nutrients present in each of the list of the grocery items that are available for purchase at the grocery store. The food budget manager 228 retrieves the user nutritional profile from the user health profile 212. The user nutritional profile may include the nutrient(s)s that may impact the user health condition(s). Upon the selection of a grocery item by a user, the food budget manager 228 determines whether the selected grocery items include nutrient(s) that are detailed in the user nutritional profile. In an embodiment, if the food budget manager 228 determines one or more of the nutrient(s) detailed in the nutritional profile is present in the selected grocery item, the food budget manager 228 identifies substitute grocery items that do not include the nutrient(s) in the user nutritional profile or a relatively lower amount of the nutrient(s) in the use nutritional profile for purchase. In an embodiment, if the food budget manager 228 identifies multiple substitute grocery items that that do not include the nutrient(s) in the user nutritional profile or a relatively lower amount of the nutrient(s) in the use nutritional profile, the food budget manager 228 recommends the substitute grocery item from the identified multiple substitute grocery items having the lowest grocery item price.

Detailed Description of Exemplary Aspects

Figure 4:
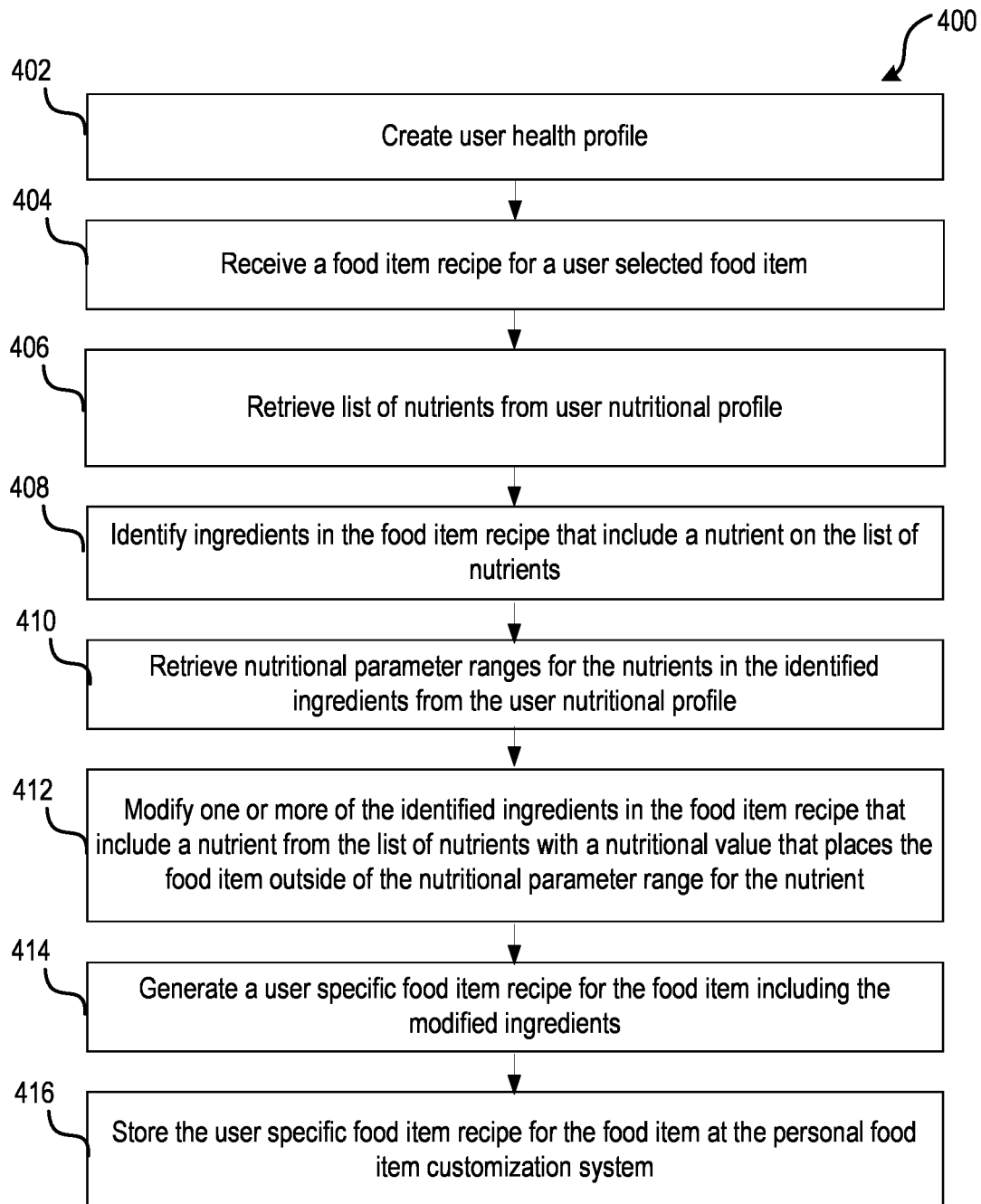
FIG. 4 is a flow diagram representation of an example of a method of customizing a food item recipe using an embodiment of a personal food item customization system.

Referring now to FIG. 4, a flow diagram representation of an example of a method 400 of customizing a food item recipe for a food item using an embodiment of a personal food item customization system 102 is shown. A personal food item customization system 102 creates a user health profile 212 at 402. The user health profile 212 may include a user identifier, user specific parameters, one or more user health conditions, and a user nutritional profile. The user provides the user identifier and the use specific parameters to the personal food item customization system 102 via the user computing device 104.

The personal food item customization system 102 retrieves the user health condition(s) and recommended nutritional parameters for nutritional values of nutrients that may impact the user health condition(s) from a health care provider system 106 affiliated with a health care provider associated with the user. The personal food item customization system 102 stores the user health condition(s) in the user health profile 212 and the recommended nutritional parameters for nutritional values of nutrients that may impact the user health condition(s) in the user nutritional profile maintained at the user health profile 212. The user nutritional profile may include a list of the nutrients that may potentially impact the user health condition(s).

The personal food item customization system 102 receives a food item recipe for a food item selected by the user from a food recipe system 108 at 404. The food item recipe may include one or more ingredients used to prepare the food item. The personal food item customization system 102 retrieves the list of nutrients that may potentially impact the user health condition(s) from the user nutritional profile at 406, identifies one or more ingredients in the food item recipe that include a nutrient from the retrieved list of nutrients at 408, and retrieves the nutritional parameter ranges for the nutrient(s) present in the identified ingredients from the user nutritional profile at 410.

The personal food item customization system 102 modifies one or more of the identified ingredients in the food item recipe that include a nutritional value for a nutrient on the list of nutrients that places the food item outside of the nutritional parameter range for the nutrient at 412. In an embodiment, the personal food item customization system 102 replaces the one or more of the ingredients in the food item recipe that include the nutrient with a substitute ingredient. The substitute ingredient reduces the amount of the nutrient in the food item and brings the food item within the nutritional parameter range for the nutrient. According to an embodiment, the personal food item customization system 102 reduces the amount of one or more of the ingredients in the food item recipe that includes the nutrient. The reduction of the amount of the one or more ingredients in the food item brings the food item within the nutritional parameter range for the nutrient. The personal food item customization system 102 generates a user specific food item recipe for the food item including the modified ingredients at 414 and stores the user specific food item recipe at the personal food item customization system 102 at 416.

Figure 5:
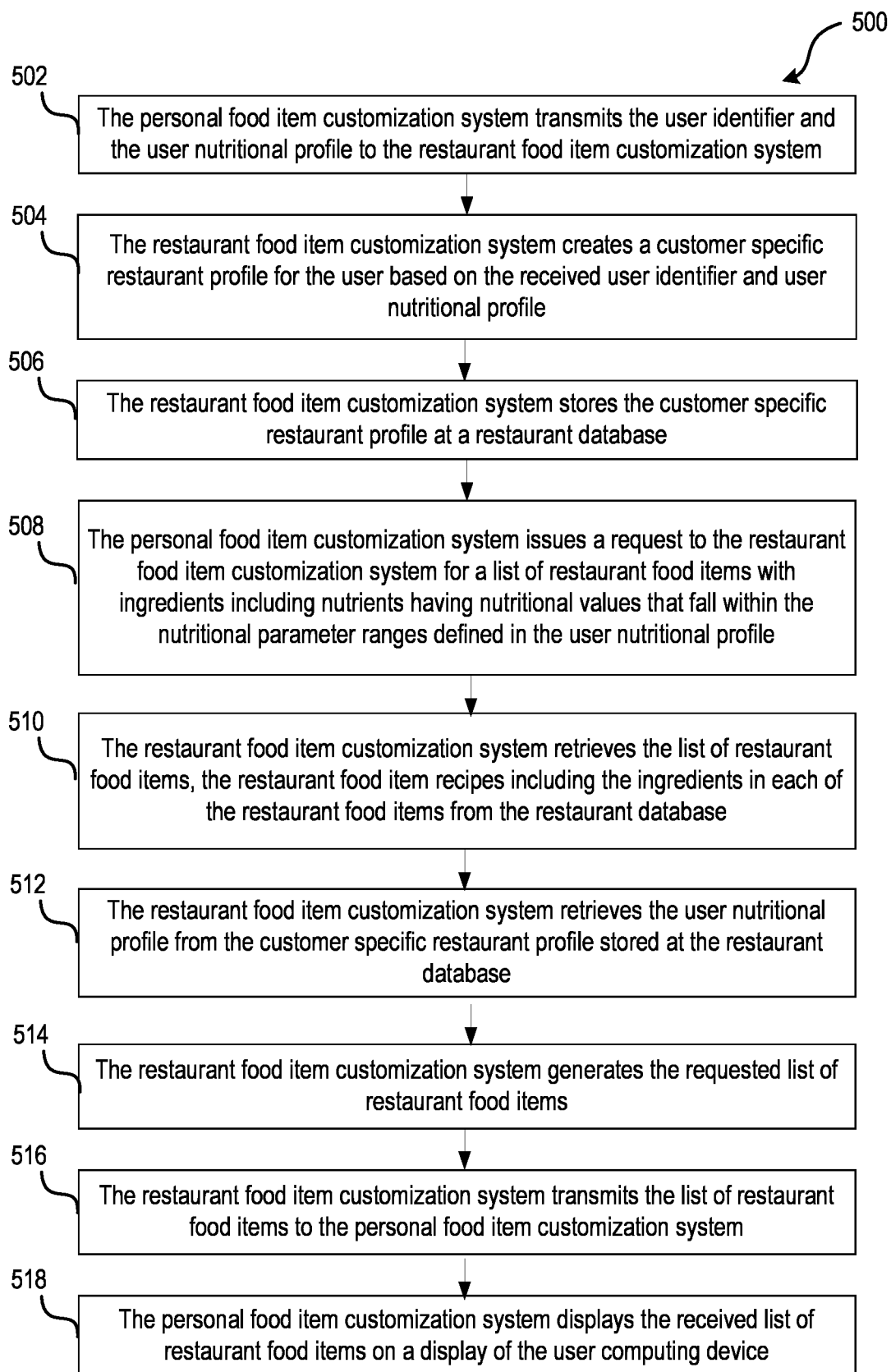
FIG. 5 is a flow diagram representation of an example of a method of using an embodiment of a personal food item customization system to coordinate with an embodiment of a restaurant food item customization system.

Referring to FIG. 5, a flow diagram representation of an example of a method 500 of using an embodiment of a personal food item customization system 102 to coordinate with an embodiment of a restaurant food item customization system 112 is shown. The personal food item customization system 102 transmits portions of the user health profile to the restaurant food item customization system 112 at an initial step 502. In an embodiment, the personal food item customization system 102 transmits the user identifier and the user nutritional profile to the restaurant food item customization system 112. The restaurant food item customization system 112 creates a customer specific restaurant profile for the user based on the received user identifier and user nutritional profile at a next step 504 and stores the customer specific restaurant profile at the restaurant database 306 at next step 506.

At step 508, the personal food item customization system 102 issues a request to the restaurant food item customization system 112 for a list of the restaurant food items with ingredients including nutrients having nutritional values that fall within the nutritional parameter range defined in the previously submitted user nutritional profile. The restaurant food item customization system 112 retrieves list of restaurant food items and the restaurant food item recipes including the ingredients in the restaurant food items from the restaurant database 306 at step 510 and retrieves the user nutritional profile from the customer specific restaurant profile stored at the restaurant database 306 at step 512.

The restaurant food item customization system 102 generates the requested list of restaurant food items at step 514. In an embodiment, the restaurant food item customization system 112 generates a list of restaurant food items with ingredients including nutrients having nutritional values that fall within the nutritional parameter range defined in the user nutritional profile. In an embodiment, the restaurant food item customization system 112 generates a list of restaurant food items with ingredients that can be modified by the restaurant to place the restaurant food items within the nutritional parameter range defined in the user nutritional profile. In an embodiment, the restaurant food item customization system 112 generates a list of previously ordered restaurant food items with ingredients that can be modified by the restaurant to place the previously ordered restaurant food items within the nutritional parameter range defined in the user nutritional profile. The restaurant food item customization system 112 then transmits the list of restaurant food items to the personal food item customization system 102 at step 516. The personal food item customization system 102 may then issue a command to display the received list of restaurant food items on a display of the user computing device 104 at a final step 518.

Hardware Architecture

Generally, the techniques disclosed herein may be implemented on hardware or a combination of software and hardware. For example, they may be implemented in an operating system kernel, in a separate user process, in a library package bound into network applications, on a specially constructed machine, on an application-specific integrated circuit (ASIC), or on a network interface card.

Software/hardware hybrid implementations of at least some of the aspects disclosed herein may be implemented on a programmable network-resident machine (which should be understood to include intermittently connected network-aware machines) selectively activated or reconfigured by a computer program stored in memory. Such network devices may have multiple network interfaces that may be configured or designed to utilize different types of network communication protocols. A general architecture for some of these machines may be described herein in order to illustrate one or more exemplary means by which a given unit of functionality may be implemented. According to specific aspects, at least some of the features or functionalities of the various aspects disclosed herein may be implemented on one or more general-purpose computers associated with one or more networks, such as for example an end-user computer system, a client computer, a network server or other server system, a mobile computing device (e.g., tablet computing device, mobile phone, smartphone, laptop, or other appropriate computing device), a consumer electronic device, a music player, or any other suitable electronic device, router, switch, or other suitable device, or any combination thereof. In at least some aspects, at least some of the features or functionalities of the various aspects disclosed herein may be implemented in one or more virtualized computing environments (e.g., network computing clouds, virtual machines hosted on one or more physical computing machines, or other appropriate virtual environments).

Figure 6:
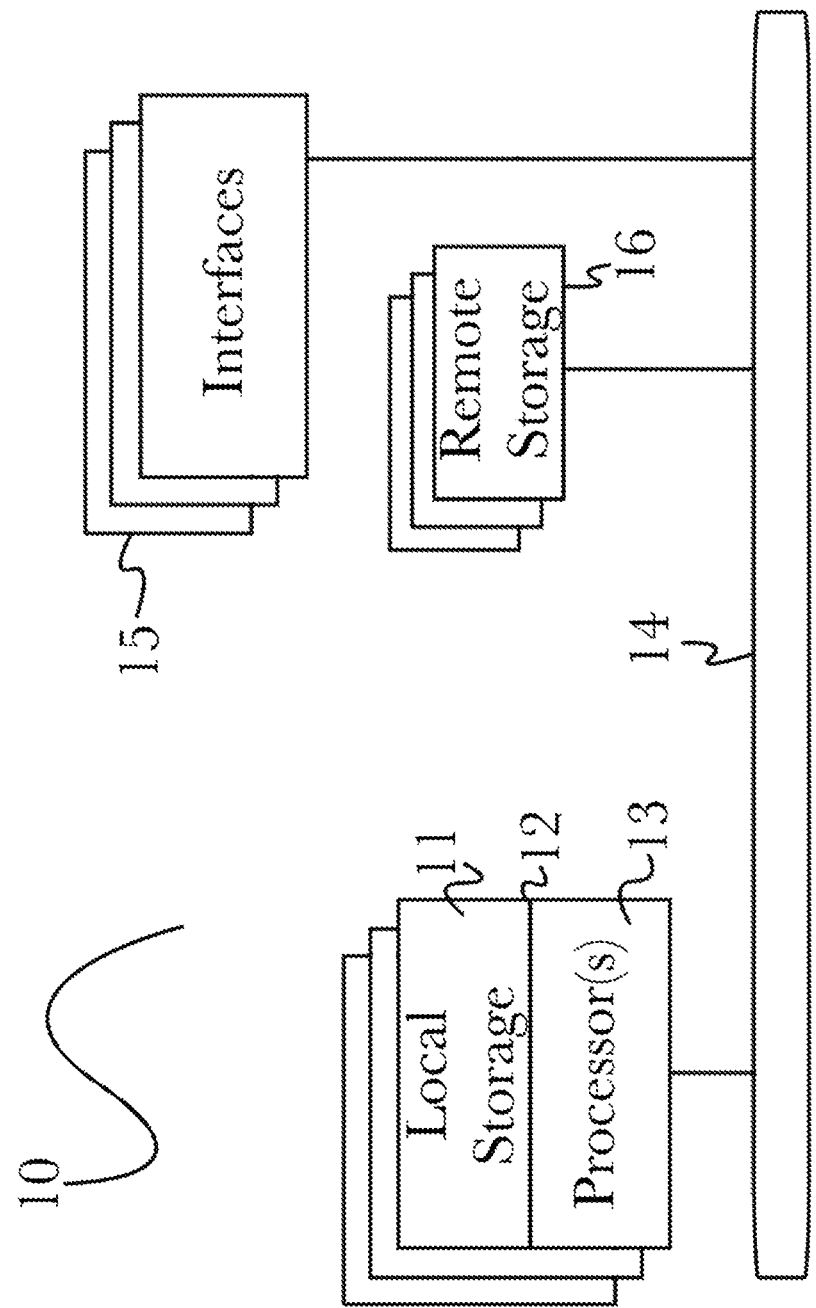
FIG. 6 is a block diagram illustrating an exemplary hardware architecture of a computing device.

Referring now to FIG. 6, there is shown a block diagram depicting an exemplary computing device 10 suitable for implementing at least a portion of the features or functionalities disclosed herein. Computing device 10 may be, for example, any one of the computing machines listed in the previous paragraph, or indeed any other electronic device capable of executing software- or hardware-based instructions according to one or more programs stored in memory. Computing device 10 may be configured to communicate with a plurality of other computing devices, such as clients or servers, over communications networks such as a wide area network a metropolitan area network, a local area network, a wireless network, the Internet, or any other network, using known protocols for such communication, whether wireless or wired.

In one aspect, computing device 10 includes one or more central processing units (CPU) 12, one or more interfaces 15, and one or more busses 14 (such as a peripheral component interconnect (PCI) bus). When acting under the control of appropriate software or firmware, CPU 12 may be responsible for implementing specific functions associated with the functions of a specifically configured computing device or machine. For example, in at least one aspect, a computing device 10 may be configured or designed to function as a server system utilizing CPU 12, local memory 11 and/or remote memory 16, and interface(s) 15. In at least one aspect, CPU 12 may be caused to perform one or more of the different types of functions and/or operations under the control of software modules or components, which for example, may include an operating system and any appropriate applications software, drivers, and the like.

CPU 12 may include one or more processors 13 such as, for example, a processor from one of the Intel, ARM, Qualcomm, and AMD families of microprocessors. In some aspects, processors 13 may include specially designed hardware such as application-specific integrated circuits (ASICs), electrically erasable programmable read-only memories (EEPROMs), field-programmable gate arrays (FPGAs), and so forth, for controlling operations of computing device 10. In a particular aspect, a local memory 11 (such as non-volatile random access memory (RAM) and/or read-only memory (ROM), including for example one or more levels of cached memory) may also form part of CPU 12. However, there are many different ways in which memory may be coupled to system 10. Memory 11 may be used for a variety of purposes such as, for example, caching and/or storing data, programming instructions, and the like. It should be further appreciated that CPU 12 may be one of a variety of system-on-a-chip (SOC) type hardware that may include additional hardware such as memory or graphics processing chips, such as a QUALCOMM SNAPDRAGON™ or SAMSUNG EXYNOS™ CPU as are becoming increasingly common in the art, such as for use in mobile devices or integrated devices.

As used herein, the term "processor" is not limited merely to those integrated circuits referred to in the art as a processor, a mobile processor, or a microprocessor, but broadly refers to a microcontroller, a microcomputer, a programmable logic controller, an application-specific integrated circuit, and any other programmable circuit.

In one aspect, interfaces 15 are provided as network interface cards (NICs). Generally, NICs control the sending and receiving of data packets over a computer network; other types of interfaces 15 may for example support other peripherals used with computing device 10. Among the interfaces that may be provided are Ethernet interfaces, frame relay interfaces, cable interfaces, DSL interfaces, token ring interfaces, graphics interfaces, and the like. In addition, various types of interfaces may be provided such as, for example, universal serial bus (USB), Serial, Ethernet, FIREWIRE™, THUNDERBOLT™, PCI, parallel, radio frequency (RF), BLUETOOTH™, near-field communications (e.g., using near-field magnetics), 802.11 (WiFi), frame relay, TCP/IP, ISDN, fast Ethernet interfaces, Gigabit Ethernet interfaces, Serial ATA (SATA) or external SATA (ESATA) interfaces, high-definition multimedia interface (HDMI), digital visual interface (DVI), analog or digital audio interfaces, asynchronous transfer mode (ATM) interfaces, high-speed serial interface (HSSI) interfaces, Point of Sale (POS) interfaces, fiber data distributed interfaces (FDDIs), and the like. Generally, such interfaces 15 may include physical ports appropriate for communication with appropriate media. In some cases, they may also include an independent processor (such as a dedicated audio or video processor, as is common in the art for high-fidelity AN hardware interfaces) and, in some instances, volatile and/or non-volatile memory (e.g., RAM).

Although the system shown in FIG. 6 illustrates one specific architecture for a computing device 10 for implementing one or more of the aspects described herein, it is by no means the only device architecture on which at least a portion of the features and techniques described herein may be implemented. For example, architectures having one or any number of processors 13 may be used, and such processors 13 may be present in a single device or distributed among any number of devices. In one aspect, a single processor 13 handles communications as well as routing computations, while in other aspects a separate dedicated communications processor may be provided. In various aspects, different types of features or functionalities may be implemented in a system according to the aspect that includes a client device (such as a tablet device or smartphone running client software) and server systems (such as a server system described in more detail below).

Regardless of network device configuration, the system of an aspect may employ one or more memories or memory modules (such as, for example, remote memory block 16 and local memory 11) configured to store data, program instructions for the general-purpose network operations, or other information relating to the functionality of the aspects described herein (or any combinations of the above). Program instructions may control execution of or comprise an operating system and/or one or more applications, for example. Memory 16 or memories 11, 16 may also be configured to store data structures, configuration data, encryption data, historical system operations information, or any other specific or generic non-program information described herein.

Because such information and program instructions may be employed to implement one or more systems or methods described herein, at least some network device aspects may include nontransitory machine-readable storage media, which, for example, may be configured or designed to store program instructions, state information, and the like for performing various operations described herein. Examples of such nontransitory machine-readable storage media include, but are not limited to, magnetic media such as hard disks, floppy disks, and magnetic tape; optical media such as CD-ROM disks; magneto-optical media such as optical disks, and hardware devices that are specially configured to store and perform program instructions, such as read-only memory devices (ROM), flash memory (as is common in mobile devices and integrated systems), solid state drives (SSD) and "hybrid SSD" storage drives that may combine physical components of solid state and hard disk drives in a single hardware device (as are becoming increasingly common in the art with regard to personal computers), memristor memory, random access memory (RAM), and the like. It should be appreciated that such storage means may be integral and non-removable (such as RAM hardware modules that may be soldered onto a motherboard or otherwise integrated into an electronic device), or they may be removable such as swappable flash memory modules (such as "thumb drives" or other removable media designed for rapidly exchanging physical storage devices), "hot-swappable" hard disk drives or solid state drives, removable optical storage discs, or other such removable media, and that such integral and removable storage media may be utilized interchangeably. Examples of program instructions include both object code, such as may be produced by a compiler, machine code, such as may be produced by an assembler or a linker, byte code, such as may be generated by for example a JAVA™ compiler and may be executed using a Java virtual machine or equivalent, or files containing higher level code that may be executed by the computer using an interpreter (for example, scripts written in Python, Perl, Ruby, Groovy, or any other scripting language).

Figure 7:
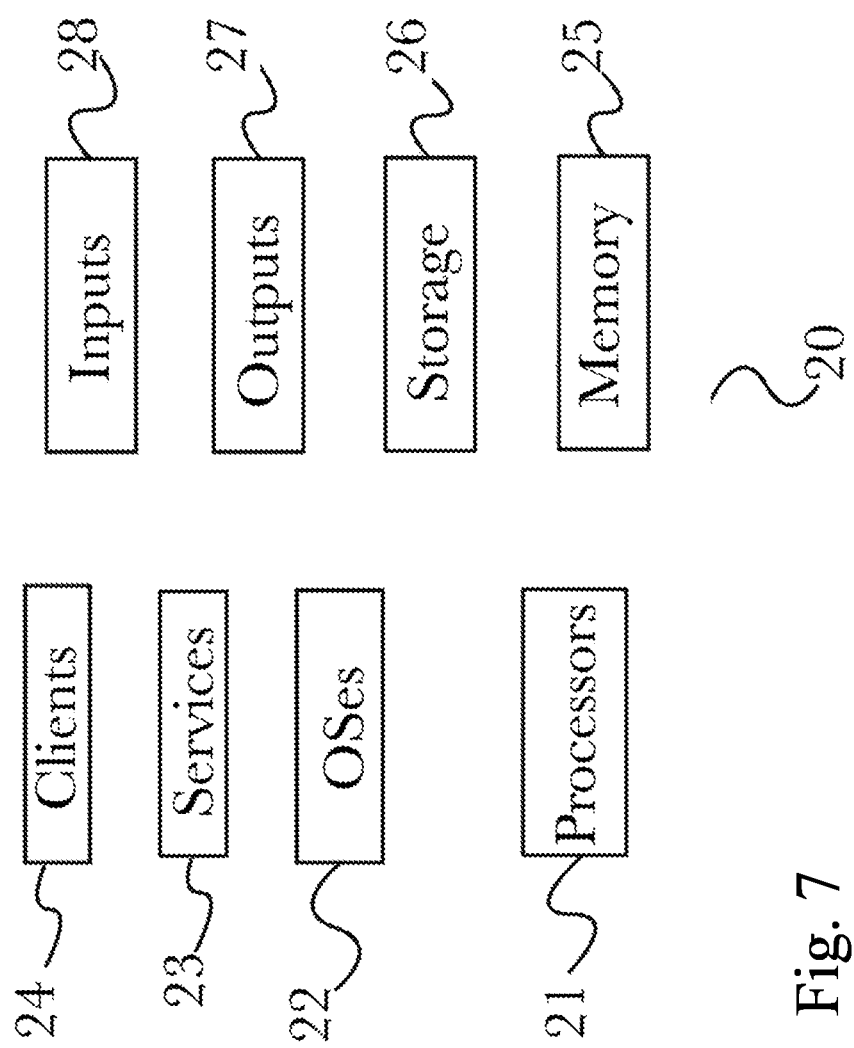
FIG. 7 is a block diagram illustrating an exemplary logical architecture for a client device.

In some aspects, systems may be implemented on a standalone computing system. Referring now to FIG. 7, there is shown a block diagram depicting a typical exemplary architecture of one or more aspects or components thereof on a standalone computing system. Computing device 20 includes processors 21 that may run software that carry out one or more functions or applications of aspects, such as for example a client application 24. Processors 21 may carry out computing instructions under control of an operating system 22 such as, for example, a version of MICROSOFT WINDOWS™ operating system, APPLE macOS™ or iOS™ operating systems, some variety of the Linux operating system, ANDROID™ operating system, or the like. In many cases, one or more shared services 23 may be operable in system 20, and may be useful for providing common services to client applications 24. Services 23 may for example be WINDOWS™ services, user-space common services in a Linux environment, or any other type of common service architecture used with operating system 21. Input devices 28 may be of any type suitable for receiving user input, including for example a keyboard, touchscreen, microphone (for example, for voice input), mouse, touchpad, trackball, or any combination thereof. Output devices 27 may be of any type suitable for providing output to one or more users, whether remote or local to system 20, and may include for example one or more screens for visual output, speakers, printers, or any combination thereof. Memory 25 may be random-access memory having any structure and architecture known in the art, for use by processors 21, for example to run software. Storage devices 26 may be any magnetic, optical, mechanical, memristor, or electrical storage device for storage of data in digital form (such as those described above, referring to FIG. 9). Examples of storage devices 26 include flash memory, magnetic hard drive, CD-ROM, and/or the like.

Figure 8:
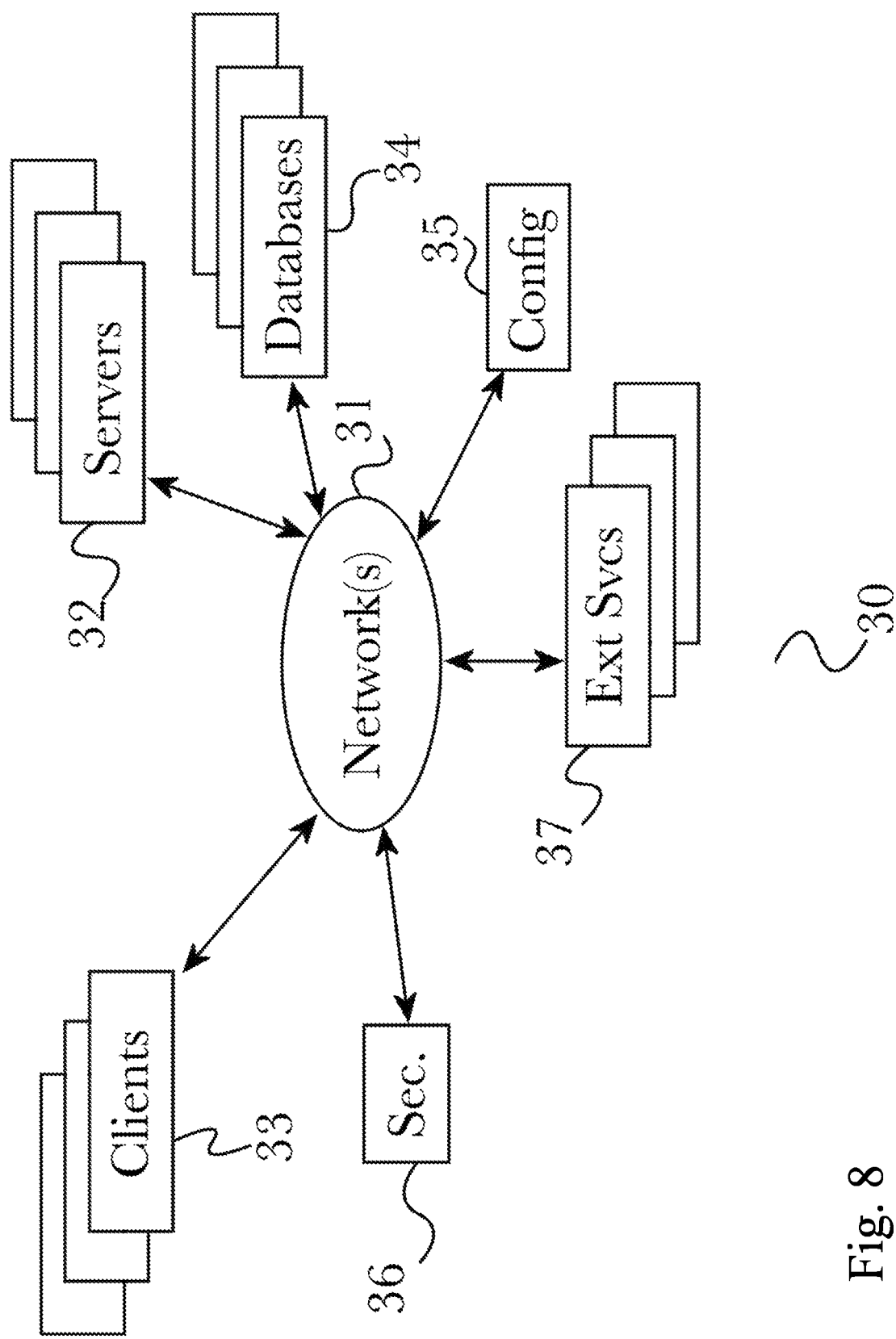
FIG. 8 is a block diagram showing an exemplary architectural arrangement of clients, servers, and external services.

In some aspects, systems may be implemented on a distributed computing network, such as one having any number of clients and/or servers. Referring now to FIG. 8, there is shown a block diagram depicting an exemplary architecture 30 for implementing at least a portion of a system according to one aspect on a distributed computing network. According to the aspect, any number of clients 33 may be provided. Each client 33 may run software for implementing client-side portions of a system; clients may comprise a system 20 such as that illustrated in FIG. 10. In addition, any number of servers 32 may be provided for handling requests received from one or more clients 33. Clients 33 and servers 32 may communicate with one another via one or more electronic networks 31, which may be in various aspects any of the Internet, a wide area network, a mobile telephony network (such as CDMA or GSM cellular networks), a wireless network (such as WiFi, WiMAX, LTE, and so forth), or a local area network (or indeed any network topology known in the art; the aspect does not prefer any one network topology over any other). Networks 31 may be implemented using any known network protocols, including for example wired and/or wireless protocols.

In addition, in some aspects, servers 32 may call external services 37 when needed to obtain additional information, or to refer to additional data concerning a particular call. Communications with external services 37 may take place, for example, via one or more networks 31. In various aspects, external services 37 may comprise web-enabled services or functionality related to or installed on the hardware device itself. For example, in one aspect where client applications 24 are implemented on a smartphone or other electronic device, client applications 24 may obtain information stored in a server system 32 in the cloud or on an external service 37 deployed on one or more of a particular enterprise's or user's premises. In addition to local storage on servers 32, remote storage 38 may be accessible through the network(s) 31.

In some aspects, clients 33 or servers 32 (or both) may make use of one or more specialized services or appliances that may be deployed locally or remotely across one or more networks 31. For example, one or more databases 34 in either local or remote storage 38 may be used or referred to by one or more aspects. It should be understood by one having ordinary skill in the art that databases in storage 34 may be arranged in a wide variety of architectures and using a wide variety of data access and manipulation means. For example, in various aspects one or more databases in storage 34 may comprise a relational database system using a structured query language (SQL), while others may comprise an alternative data storage technology such as those referred to in the art as "NoSQL" (for example, HADOOP CASSANDRA™, GOOGLE BIGTABLE™, and so forth). In some aspects, variant database architectures such as column-oriented databases, in-memory databases, clustered databases, distributed databases, or even flat file data repositories may be used according to the aspect. It will be appreciated by one having ordinary skill in the art that any combination of known or future database technologies may be used as appropriate, unless a specific database technology or a specific arrangement of components is specified for a particular aspect described herein. Moreover, it should be appreciated that the term "database" as used herein may refer to a physical database machine, a cluster of machines acting as a single database system, or a logical database within an overall database management system. Unless a specific meaning is specified for a given use of the term "database", it should be construed to mean any of these senses of the word, all of which are understood as a plain meaning of the term "database" by those having ordinary skill in the art.

Similarly, some aspects may make use of one or more security systems 36 and configuration systems 35. Security and configuration management are common information technology (IT) and web functions, and some amount of each are generally associated with any IT or web systems. It should be understood by one having ordinary skill in the art that any configuration or security subsystems known in the art now or in the future may be used in conjunction with aspects without limitation, unless a specific security 36 or configuration system 35 or approach is specifically required by the description of any specific aspect.

Figure 9:
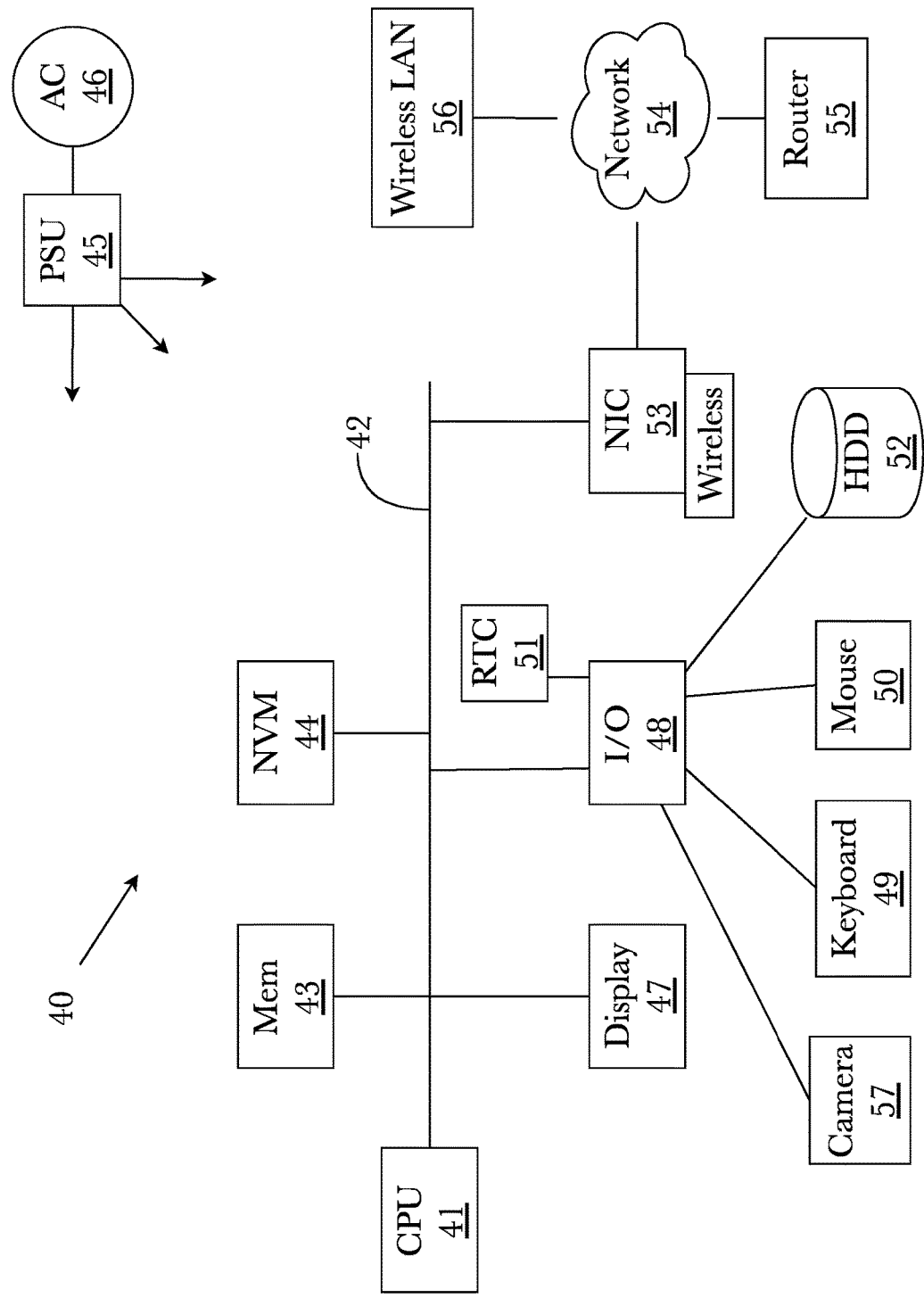
FIG. 9 is another block diagram illustrating an exemplary hardware architecture of a computing device.

FIG. 9 shows an exemplary overview of a computer system 40 as may be used in any of the various locations throughout the system. It is exemplary of any computer that may execute code to process data. Various modifications and changes may be made to computer system 40 without departing from the broader scope of the system and method disclosed herein. Central processor unit (CPU) 41 is connected to bus 42, to which bus is also connected memory 43, nonvolatile memory 44, display 47, input/output (I/O) unit 48, and network interface card (NIC) 53. I/O unit 48 may, typically, be connected to peripherals such as a keyboard 49, pointing device 50, hard disk 52, real-time clock 51, a camera 57, and other peripheral devices. NIC 53 connects to network 54, which may be the Internet or a local network, which local network may or may not have connections to the Internet. The system may be connected to other computing devices through the network via a router 55, wireless local area network 56, or any other network connection. Also shown as part of system 40 is power supply unit 45 connected, in this example, to a main alternating current (AC) supply 46. Not shown are batteries that could be present, and many other devices and modifications that are well known but are not applicable to the specific novel functions of the current system and method disclosed herein. It should be appreciated that some or all components illustrated may be combined, such as in various integrated applications, for example Qualcomm or Samsung system-on-a-chip (SOC) devices, or whenever it may be appropriate to combine multiple capabilities or functions into a single hardware device (for instance, in mobile devices such as smartphones, video game consoles, in-vehicle computer systems such as navigation or multimedia systems in automobiles, or other integrated hardware devices).

In various aspects, functionality for implementing systems or methods of various aspects may be distributed among any number of client and/or server components. For example, various software modules may be implemented for performing various functions in connection with the system of any particular aspect, and such modules may be variously implemented to run on server and/or client components.

The skilled person will be aware of a range of possible modifications of the various aspects described above. Accordingly, the present invention is defined by the claims and their equivalents.

What is claimed is:

1. A personal food item customization system, comprising:
    a user health profile manager comprising a plurality of programming instructions stored in a memory of, and operable on a processor of, a computing device, wherein the plurality of programming instructions, when operating on the processor, cause the computing device to:
        create a user health profile for a user comprising a plurality of user health conditions and a plurality of nutritional parameter ranges, wherein each nutritional parameter range comprises a range of nutritional values for a particular nutrient determined by the plurality of user health conditions;
    a food item recipe ingredient manager comprising a plurality of programming instructions stored in a memory of, and operable on a processor of, a computing device, wherein the plurality of programming instructions, when operating on the processor, cause the computing device to:
        provide a food item list identifying the food items that can be modified by a restaurant to place the food items within the nutritional parameter ranges associated with the nutrients defined in the user health profile;
        receive a food item recipe associated with a food item, the food item recipe to be prepared in the restaurant and comprising a plurality of ingredients;
        identify at least one ingredient from the plurality of ingredients in the food item recipe that includes a nutritional value for the particular nutrient defined by the user health condition, wherein the at least one identified ingredient places the food item outside of the nutritional parameter range;
        modify one or more of the at least one identified ingredient to bring the nutritional value within the nutritional parameter range; and
        generate a user specific food item recipe comprising the at least one modified ingredients.

2. The system of claim 1, further wherein the food item recipe ingredient manager modifies one of the at least one identified ingredients by replacing with a substitute ingredient.

3. The system of claim 1, further wherein the food item recipe ingredient manager modifies the at least one identified ingredient by reducing an amount of the at least one identified ingredient.

4. The system of claim 1, further comprising a food item preparation technique manager comprising a plurality of programming instructions stored in a memory of, and operable on a processor of, a computing device, wherein the plurality of programming instructions, when operating on the processor, cause the computing device to:
- identify a food item preparation technique;
- determine whether the food item preparation technique places the nutritional value of the nutrient in the food item outside of the nutritional parameter range; and
- modify the food item preparation technique based on the determination.

5. The system of claim 1, further wherein the food item recipe ingredient manager:
- determines whether addition of a potential ingredient will positively impact the user health condition; and
- adds the potential ingredient to the plurality of food ingredients based on the determination.

6. The system of claim 1, further comprising a biometric data manager comprising a plurality of programming instructions stored in a memory of, and operable on a processor of, a computing device, wherein the plurality of programming instructions, when operating on the processor, cause the computing device to:
- receive user biometric data;
- determine whether the received user biometric data impacts the nutritional parameter range in the user health profile; and
- update the nutritional parameter range in accordance with the received biometric data based on the determination.

7. The system of claim 6, further wherein the biometric data manager:
- receives pre-meal user biometric data prior to a user's consumption of a food item prepared in accordance with a user specific food item recipe;
- receives a post-meal user biometric data following the user's consumption of the food item prepared in accordance with the user specific food item recipe;
- performs a first comparison of the pre-meal user biometric data with a pre-meal biometric data threshold;
- performs a second comparison of the post-meal user biometric data with a post-meal biometric data threshold; and
- provides biometric feedback data based on the first and second comparisons.

8. The system of claim 1, further comprising a restaurant food item manager comprising a plurality of programming instructions stored in a memory of, and operable on a processor of, a computing device, wherein the plurality of programming instructions, when operating on the processor, cause the computing device to:
- establish a communication channel between the personal food item customization system and a restaurant customer food item customization system, the restaurant customer food item customization system comprising a plurality of restaurant food items;
- transmit at least a portion of the user health profile from the personal food item customization system to the restaurant customer food item customization system; and
- receive, from the restaurant food item customization system, a restaurant food item list identifying a plurality of restaurant food items that include a nutritional value for a nutrient within the nutritional parameter range.

9. The system of claim 8, further wherein the restaurant food item manager:
- transmits at least a portion of the user health profile to the restaurant customer food item customization system for addition to a customer specific restaurant profile at the restaurant food item customization system.

10. The system of claim 8, further wherein the restaurant food item manager:
- transmits at least a portion of the user health profile to the restaurant customer food item customization system for addition to a customer specific restaurant profile at the restaurant food item customization system, the customer specific restaurant profile including a list of previously ordered food items; and
- receives the list of the previously ordered food items identifying the previously ordered restaurant food items that can be modified by the restaurant such that the modified restaurant food items include a nutritional value for a nutrient within the nutritional parameter range.

11. A method for utilizing a personal food item customization system, comprising the steps of:
- creating, at a user health profile manager, a user health profile for a user comprising a plurality of user health conditions and a plurality of nutritional parameter ranges, wherein each nutritional parameter range comprises a range of nutritional values for a particular nutrient determined by the plurality of user health conditions;
- providing a food item list identifying the food items that can be modified by a restaurant to place the food items within the nutritional parameter ranges associated with the nutrients defined in the user health profile;
- receiving, at a food item recipe ingredient manager, a food item recipe associated with a food item, the food item recipe to be prepared in the restaurant and comprising a plurality of ingredients;
- identifying at least one ingredient from the plurality of ingredients in the food item recipe that includes a nutritional value for the particular nutrient defined by the user health condition, wherein the at least one identified ingredient places the food item outside of the nutritional parameter range;
- modifying one or more of the at least one identified ingredient to bring the nutritional value within the nutritional parameter range; and
- generating a user specific food item recipe comprising the at least one modified ingredients.

12. The method of claim 11, further wherein the food item recipe ingredient manager modifies one of the at least one identified ingredients by replacing with a substitute ingredient.

13. The method of claim 11, further wherein the food item recipe ingredient manager modifies the at least one identified ingredient by reducing an amount of the at least one identified ingredient.

14. The method of claim 11, further comprising the steps of:
- identifying, at a food item preparation technique manager, a food item preparation technique;
- determining whether the food item preparation technique places the nutritional value of the nutrient in the food item outside of the nutritional parameter range; and
- modifying the food item preparation technique based on the determination.

15. The method of claim 11, further comprising the steps of:
- determining whether addition of a potential ingredient will positively impact the user health condition; and
- adding the potential ingredient to the plurality of food ingredients based on the determination.

16. The method of claim 11, further comprising the steps of:
- receiving, at a biometric data manager, user biometric data;
- determining whether the received user biometric data impacts the nutritional parameter range in the user health profile; and
- updating the nutritional parameter range in accordance with the received biometric data based on the determination.

17. The method of claim 16, further comprising the steps of:
- receiving pre-meal user biometric data prior to a user's consumption of a food item prepared in accordance with a user specific food item recipe;
- receiving a post-meal user biometric data following the user's consumption of the food item prepared in accordance with the user specific food item recipe;
- performing a first comparison of the pre-meal user biometric data with a pre-meal biometric data threshold;
- performing a second comparison of the post-meal user biometric data with a post-meal biometric data threshold; and
- providing biometric feedback data based on the first and second comparisons.

18. The method of claim 11, further comprising the steps of:
- establishing, at a restaurant food item manager, a communication channel between the personal food item customization system and a restaurant customer food item customization system, the restaurant customer food item customization system comprising a plurality of restaurant food items;
- transmitting at least a portion of the user health profile from the personal food item customization system to the restaurant customer food item customization system; and
- receiving, from the restaurant food item customization system, a restaurant food item list identifying a plurality of restaurant food items that include a nutritional value for a nutrient within the nutritional parameter range.

19. The method of claim 18, further comprising the steps of:
- transmitting at least a portion of the user health profile to the restaurant customer food item customization system for addition to a customer specific restaurant profile at the restaurant food item customization system.

20. The method of claim 18, further comprising the steps of:
- transmitting at least a portion of the user health profile to the restaurant customer food item customization system for addition to a customer specific restaurant profile at the restaurant food item customization system, the customer specific restaurant profile including a list of previously ordered food items; and
- receiving the list of the previously ordered food items identifying the previously ordered restaurant food items that can be modified by the restaurant such that the modified restaurant food items include a nutritional value for a nutrient within the nutritional parameter range.

* * * * *